US006359061B1

(12) United States Patent
Swayze et al.

(10) Patent No.: US 6,359,061 B1
(45) Date of Patent: *Mar. 19, 2002

(54) AMIDE COMPOUND LIBRARIES

(75) Inventors: Eric Edward Swayze, Carlsbad; Peter William Davis, Encinitas, both of CA (US)

(73) Assignee: ISIS Pharmaceuticals, Inc., Carlsbad, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/272,106

(22) Filed: Mar. 19, 1999

(51) Int. Cl.[7] .................... C07D 211/72; C07D 211/84; C08G 63/91

(52) U.S. Cl. .................... 525/54.11; 514/579; 546/316; 548/228; 548/229; 548/316.4; 548/336.1; 548/338.1; 548/338.5; 548/477; 548/497; 558/390; 558/430; 558/438; 558/442; 540/148; 540/158; 564/1; 564/50; 564/105; 544/358

(58) Field of Search .................... 514/579; 546/316; 544/358; 548/228, 229, 316.4, 336.1, 338.1, 338.5, 477, 497; 525/54.11; 558/390, 430, 438, 442; 560/148, 158; 564/1, 50, 105

(56) References Cited

U.S. PATENT DOCUMENTS

| 5,539,083 A | 7/1996 | Cook et al. .................. 530/333 |
| 5,831,014 A | 11/1998 | Cook et al. .................. 530/350 |

OTHER PUBLICATIONS

Dueholm et al., Bioorg. Med. Chem. Lett. vol. 4(8) pp 1077–1080 and RN 159411–09–3, Apr. 1994.*
Achari, A. et al., "Facing up to Membranes: Structure / Function Relationships in Phospholipases", *Cold Spring Harbor Symp. Quant. Biol.*, 1987, vol. 52, Cold Spring Harbor Laboratory, 441–452.
Atherton, E. et al., "The Fluorenylmethoxycarbonyl Amino Protecting Group", *The Peptides*, 1987, 9, 1–39.
Bomalaski, J.S. et al., "Human Extracellular Recombinant Phospholipase $A_2$ Induces an Inflamatory response in Rabbit Joints", *J. Immunol.*, 1991, 146, 3904–3910.
Brennen, T. et al., "Two–Dimensional Parallel Array Technology as a New Approach to Automated Combinatorial Solid Phase Organic Synthesis", *Biotech. & Bioengin.*, 1998, 61, 33–45.
Burack, W.R. et al., "Role of Lateral Phase Separation in the Modulation of Phospholipase $A_2$ Activity", *Biochemistry*, 1993, 32, 583–589.
Campbell, M.M. et al., "Inhibition of Phospholipase $A_2$; a Molecular Recognition Study", *J. Chem. Soc. Chem. Comm.*, 1988, 1560–1562.

Cho, W. et al., "The Chemical Basis for Interfacial Activation of Monomeric Phospholipases $A_2$", *J. Biol. Chem.*, 1988, 263, 11237–11241.
Davidson, F.F. et al., "1–Stearyl,2–Stearoylaminodeoxyphosphatidylcholine, A Potent Reversible Inhibitor of Phospholipase $A_2$", *Biochem. Biophys. Res. Comm.*, 1986, 137, 587–592.
Davidson, F.F. et al., "Inhibition of Phospholipase $A_2$ by 'Lipocortins' and Calpactins", *J. Biol. Chem.*, 1987, 262, 1698–1705.
Dennis, E.A., "Phospholipases", *The Enzymes*, Boyer, P.D. (ed.), Academic Press, New York, 1983, vol. 16, 307–353.
Franson, R. et al., "Phospholipid metabolism by phagocytic cells. Phospholipase $A_2$ associated with rabbit polymorphonuclear leukocyte granules", *J. Lipid Res.*, 1974, 15, 380–388.
Glaser, K.B. et al., "Phospholipase $A_2$ enzymes: regulation and inhibition", *TiPS*, 1993, 14, 92–98.
Grainger, D.W. et al., "An enzyme caught in action: direct imaging of hydrolytic function and domain formation of phospholipase $A_2$ in phosphatidylcholine monolayers", *FEBS Letts.*, 1989, 252, 73–82.
Lombardo, D. et al., "Cobra Venom Phospholipase $A_2$ Inhibition by Manoalide", *J. Biol. Chem.*, 1985, 260, 7234–7240.
Märki, F. et al., "Differential inhibition of human secreory and cytosolic phospholipase $A_2$", *Agents Actions*, 1993, 38, 202–211.
Miyake, A. et al., "The Novel Natural Product YM–26567–1 [(+)–trans–4–(3–dodecanoyl–2,3, 6–trihydroxyphenyl)–7–hydroxy2–(4–hydroxyphenyl)chroman]: A Competitive Inhibitor of Group II Phospholipase $A_2$", *J. Pharm. Exp. Therap.*, 1992, 263, 1302–1307.
Noel, J.P. et al., "Phospholipase $A_2$ Engineering. 3. Replacement of Lysine–56 by Neutral Residues Improves Catalytic Potency Significantly, Alters Substrate Specificity, and Clarifies the Mechanism of Interfacial Recognition", *J. Am. Chem. Soc.*, 1990, 112, 3704–3706.

(List continued on next page.)

Primary Examiner—Bennett Celsa
(74) Attorney, Agent, or Firm—Woodcock Washburn LLP

(57) ABSTRACT

Amide compounds of formula (I), combinatorial libraries of amide compounds and methods of preparing the same are provided. Libraries of the invention are useful for screening in biological assays in order to identify pharmaceutically useful compounds.

(I)

$$R_1'\underset{R_1}{\diagdown}N\underset{O}{-}\overset{R_2}{\underset{|}{C}}-N\underset{R_4}{-}\overset{}{\underset{R_3}{C}}-N\underset{R_5}{\overset{R_5'}{\diagdown}}$$

9 Claims, 8 Drawing Sheets

OTHER PUBLICATIONS

Oinuma, H. et al., "Synthesis and Biological Evaluation of Substituted Benzenesulfinamides as Novel Potent Membrane–Bound Phospholipase $A_2$ Inhibitors", *J. Med. Chem.*, 1991, 34, 2260–2267.

Pruzanski, W. et al., "Enzymatic Activity and Immunoreactivity of Extracellular Phospholipase $A_2$ in Inflammatory Synovial Fluids", *Inflamation*, 1992, 16, 451–457.

Sampson, B.A. et al., "Identification and Characterization of a New Gene of *Escherichia coli* K–12 Involved in Outer Membrane Permeability", *Genetics*, 1989, 122, 491–501.

Samukov, V.V. et al., "2–(4–Nitrophenyl) sulfonylethoxycarbonyl (Nse) Group as a Base–Libile α–Amino Protection for Solic Phase Peptide Synthesis", *Tetrahedron Letts.*, 1994, 35, 7821–7824.

Scott, D.L. et al., "Interfacial Catalysis: The Mechanism of Phospholipase $A_2$", *Science*, 1990, 250, 1541–1546.

Tanaka, K. et al., "A Novel Type of Phospholipase $A_2$ Inhibitor, Thielocin A1β, and Mechanism of Action", *J. Antibiotics*, 1992, 45, 1071–1078.

Verhart, C.G.J., "New base–labile amino–protective groups for peptide synthesis", *Recl. Trav. Chim. Pays–Bas*, 1988, 107, 621–626.

Vishwanath, B.S. et al., "Edema–Inducing Activity of Phospholipase $A_2$ Purified from Human Synovial Fluid and Inhibition by Aristolochic Acid", *Inflammation*, 1988, 12, 549–561.

Washburn, W.N. et al., "Suicide–inhibitory Bifunctionally Linked Substrates (SIBLINKS) as Phospholipase $A_2$ Inhibitors", *J. Biol. Chem.*, 1991, 266, 5042–5048.

Wery, J.P. et al., "Structure of recombinant human rheumatoid arthritic synovial fluid phospholipase $A_2$ at 2.2 Å resolution", *Nature*, 1991, 352, 79–82.

Yang, C.C. et al., "Studies on the status of lysine residues in phospholipase $A_2$ from *Naja naja atra* (Taiwan cobra) snake venom", *Biochem. J.*, 1989, 262, 855–860.

Yuan, W. et al., "Synthesis and Evaluation of Phospholipid Analogues as Inhibitors of Cobra Venom Phospholipase $A_2$", *J. Am. Chem. Soc.*, 1987, 109, 8071–8081.

U.S. application No. 08/466,395, Cook et al., filed Jun. 6, 1995.

U.S. application No. 09/131,270, Cook et al., filed Aug. 7, 1998.

* cited by examiner

AMIDE COMPOUND LIBRARIES

FIELD OF THE INVENTION

The present invention relates to diverse combinatorial libraries, processes and apparatus, in particular to diverse libraries of compounds incorporating amide scaffolds.

BACKGROUND OF THE INVENTION

Discovery of new therapeutic compounds for treating diseases has typically involved screening individual compounds against targets representative of a particular disease of interest. The iterative process relies upon finding a compound having at least a minimal level of activity in an assay and then synthesizing as many derivatives of the lead compound as possible. The derivatives tested would form the basis of a "structure-activity relationship" (SAR) which would hopefully provide insight for designing a lead compound. Often the process is repeated time and again before any lead is uncovered. The obvious and major drawback in this drug discovery process is the generation of compounds on a one-at-a-time basis requiring much labor, time and expense.

Advances in robotics and solid-phase chemical synthesis has spawned the combinatorial approach for preparing libraries of compounds which makes synthesizing thousands of diverse compounds feasible. What once took months or even years by the traditional approach has become possible in a matter of weeks and even days through combinatorial chemistry, thereby drastically reducing the time, labor and expense involved in drug discovery.

The combinatorial approach has been adapted for preparing vast libraries of oligomeric compounds such as peptides and non-oligomeric small organic molecules on the order of $10^2$ to $10^6$ discreet compounds. Theoretically the total number of compounds in a library is limited only by the number of available reagents for forming substituents on a central scaffold.

SUMMARY OF THE INVENTION

The present invention provides amide compounds of formula (I):

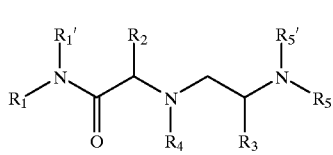

(I)

wherein:
each $R_1$, $R_{1'}$, $R_4$, $R_5$ and $R_{5'}$ is, independently, H, an amino protecting group, or $CH_2$, $CH(R_2)$, $C=O$, $C=S$, $S(=O)_2$, $C(=O)NH$, $C(=S)NH$ or $C(=O)O$ substituted with H or a hydrocarbyl group selected from $C_1$–$C_{10}$ alkyl, $C_2$–$C_{10}$ alkenyl, $C_2$–$C_{20}$ alkynyl, $C_6$–$C_{14}$ aryl, $C_6$–$C_{14}$ aralkyl, $C_3$–$C_{14}$ cycloalkyl, $C_5$–$C_{14}$ fused cycloalkyl, $C_4$–$C_{14}$ heterocycle, $C_4$–$C_{14}$ heterocyclylalkyl, $C_4$–$C_{14}$ heteroaryl, $C_4$–$C_{14}$ heteroarylalkyl and $CH(R_2)$—$NH$—$R_2$; wherein said hydrocarbyl group is optionally substituted with oxo, acyl, alkoxy, alkoxycarbonyl, alkyl, alkenyl, alkynyl, amino, amido, azido, aryl, heteroaryl, carboxylic acid, cyano, guanidino, halo, haloalkyl, haloalkoxy, hydrazino, hydroxyl, alkylsulfonyl, nitro, sulfide, sulfone, sulfonate, sulfonamide, thiol, and thioalkoxy, provided that $R_{1'}$ may also be a solid support and $R_4$ is not H; and each $R_2$ and $R_3$ is, independently, H or a hydrocarbyl group selected from $C_1$–$C_{10}$ alkyl, $C_2$–$C_{10}$ alkenyl, $C_2$–$C_{20}$ alkynyl, $C_6$–$C_{14}$ aryl, $C_6$–$C_{14}$ aralkyl, $C_3$–$C_{14}$ cycloalkyl, $C_5$–$C_{14}$ fused cycloalkyl, $C_4$–$C_{14}$ heterocyclyl, $C_4$–$C_{14}$ heterocycloalkyl, $C_4$–$C_{14}$ heteroaryl and $C_4$–$C_{14}$ heteroarylalkyl; wherein said hydrocarbyl group is optionally substituted with acyl, alkoxy, alkoxycarbonyl, alkyl, alkenyl, alkynyl, amino, amido, azido, aryl, heteroaryl, carboxylic acid, cyano, guanidino, halo, haloalkyl, haloalkoxy, hydrazino, hydroxyl, alkylsulfonyl, nitro, sulfide, sulfone, sulfonate, sulfonamide, thiol or thioalkoxy, provided that $R_2$ is not H.

The present invention also provides combinatorial libraries comprising a plurality of amide compounds of formula In another aspect of the present invention there are provided methods for preparing amide compounds of formula (I) comprising:

attaching an amine to a solid support to form a solid support-bound amine of formula (II) wherein SS is a solid support;

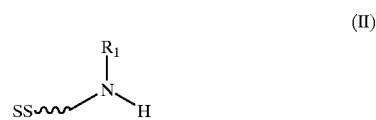

(II)

reacting compound (II) with an FMOC-protected amino acid to form an amide compound of formula (III);

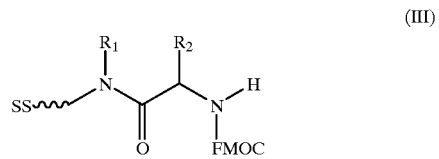

(III)

replacing the FMOC protecting group on the amino acid with a sulfonyl protecting group to form an amide compound of formula (IV);

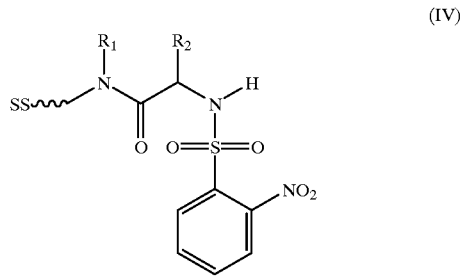

(IV)

reacting the secondary amine moiety of the compound of formula (IV) with a protected aminohydroxy compound of formula (V) wherein Pg is a protecting group;

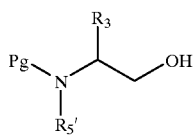
(V)

to form an amide compound of formula (VI);

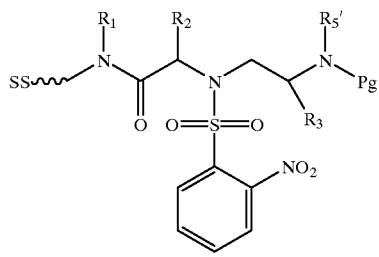
(VI)

removing the sulfonyl protecting group of the compound of formula (VI) to form an amide compound of formula (VII) bearing a protected terminal primary amine moiety and a secondary amine moiety;

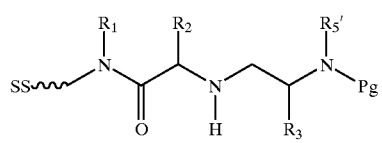
(VII)

reacting the secondary amine of the compound of formula (VII) with an $R_4$ building block to form an amide compound of formula (VIII) bearing a protected terminal primary amine moiety;

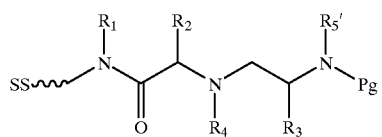
(VIII)

removing the protecting group on the terminal primary amine moiety to form an amide compound of formula (IX); and

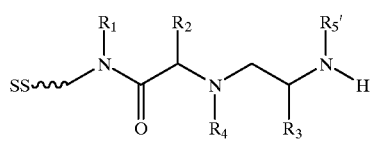
(IX)

reacting the deprotected primary amine moiety with an $R_5$ building block to form an amide compound of formula (X).

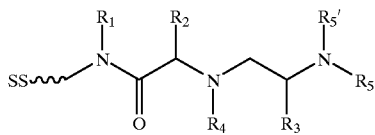
(X)

Also provided, in accordance with the present invention, are methods further comprising cleaving amide compounds of formula (X) from the solid support to form amide compounds of formula (I).

The present invention also provides pharmaceutical compositions of amide compounds of formula (I).

DETAILED DESCRIPTION OF THE INVENTION

Figure 1:
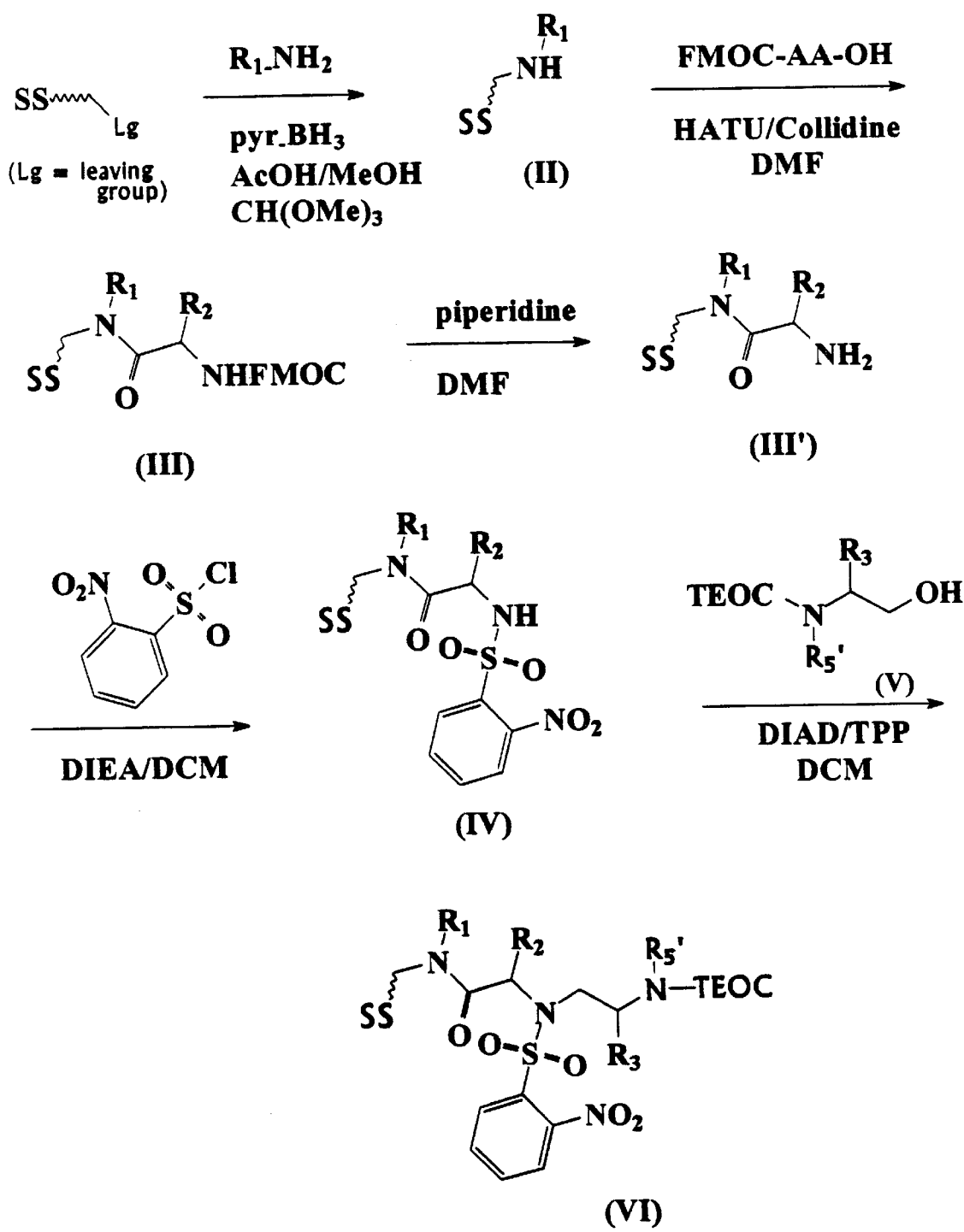
FIGS. 1 and 2 show a general scheme for the synthesis of amide compounds of formula (I).
Figure 2:
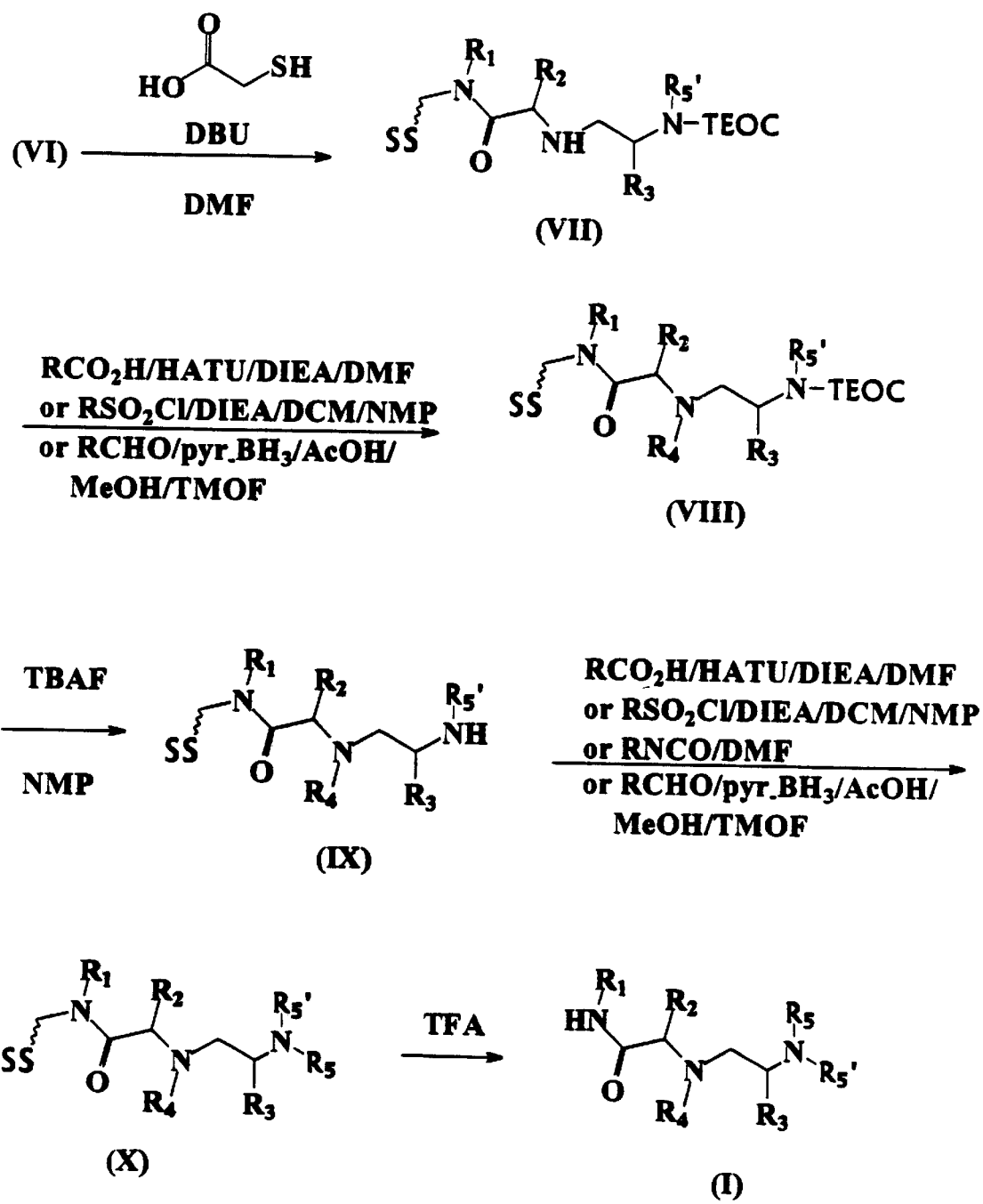
Figure 3:
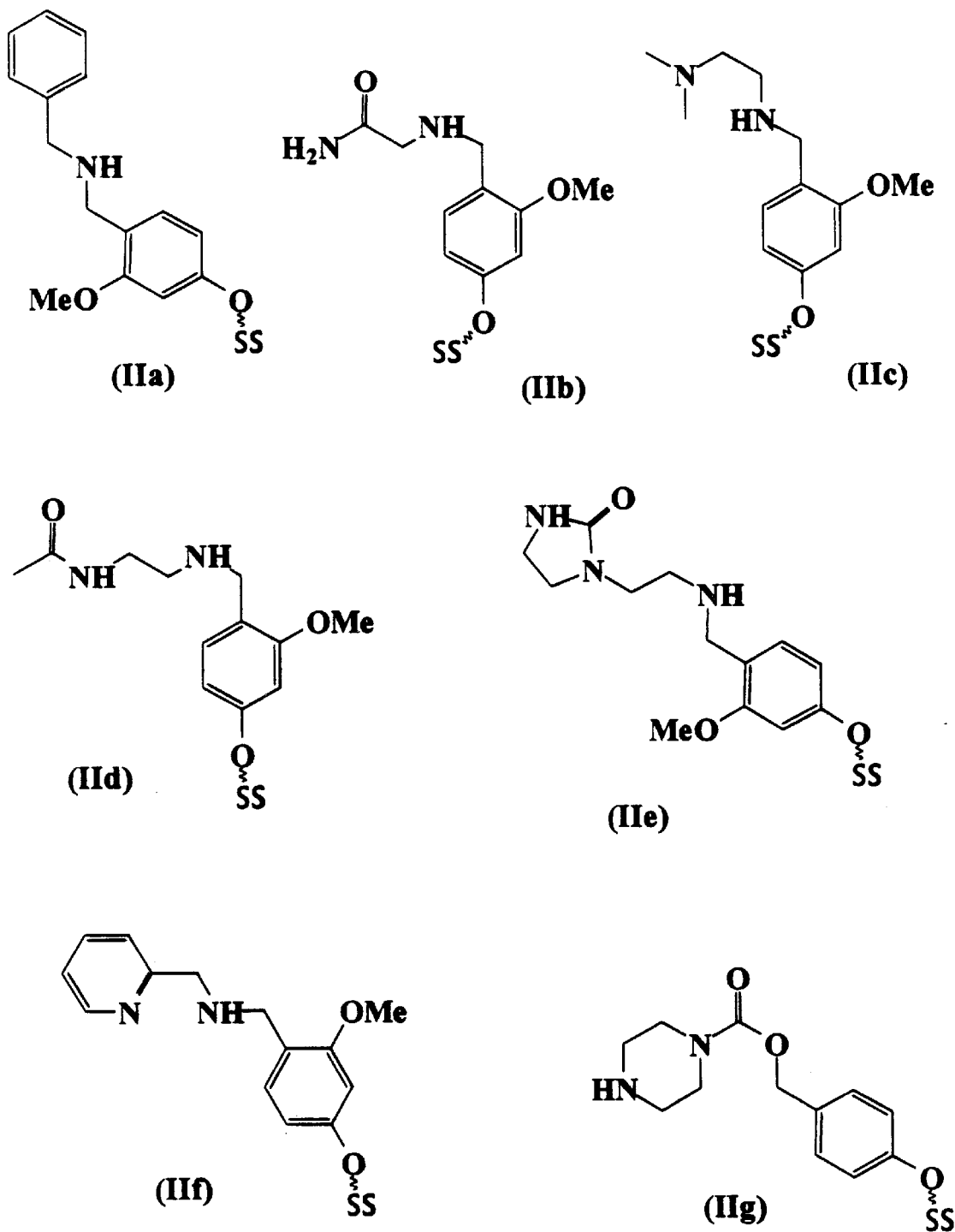
FIG. 3 shows solid-support-bound amine compounds of general formula (II).
Figure 4:
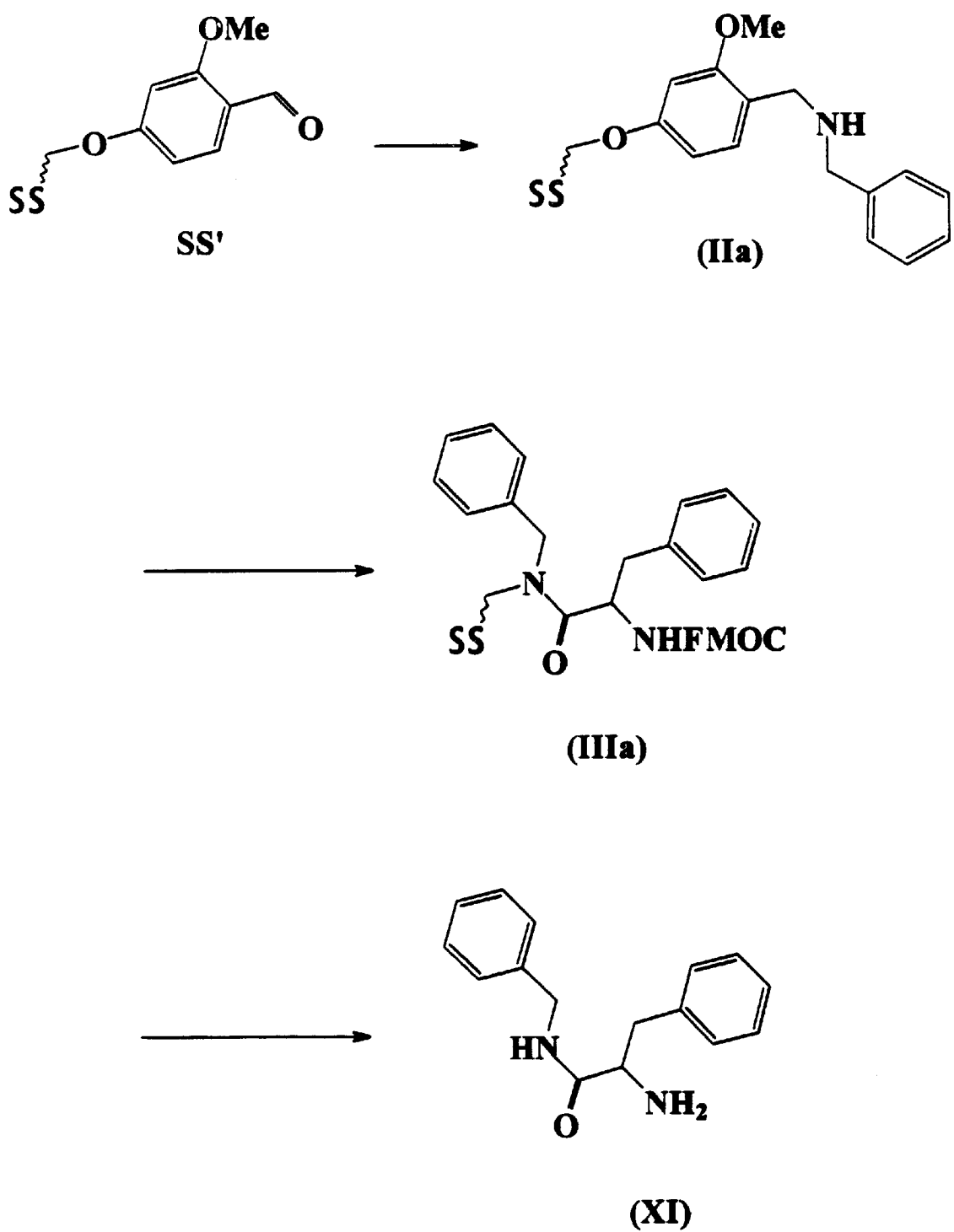
FIG. 4 shows a schematic for the synthesis of an amino acid derivative of an amide compound of formula (XI).
Figure 5:
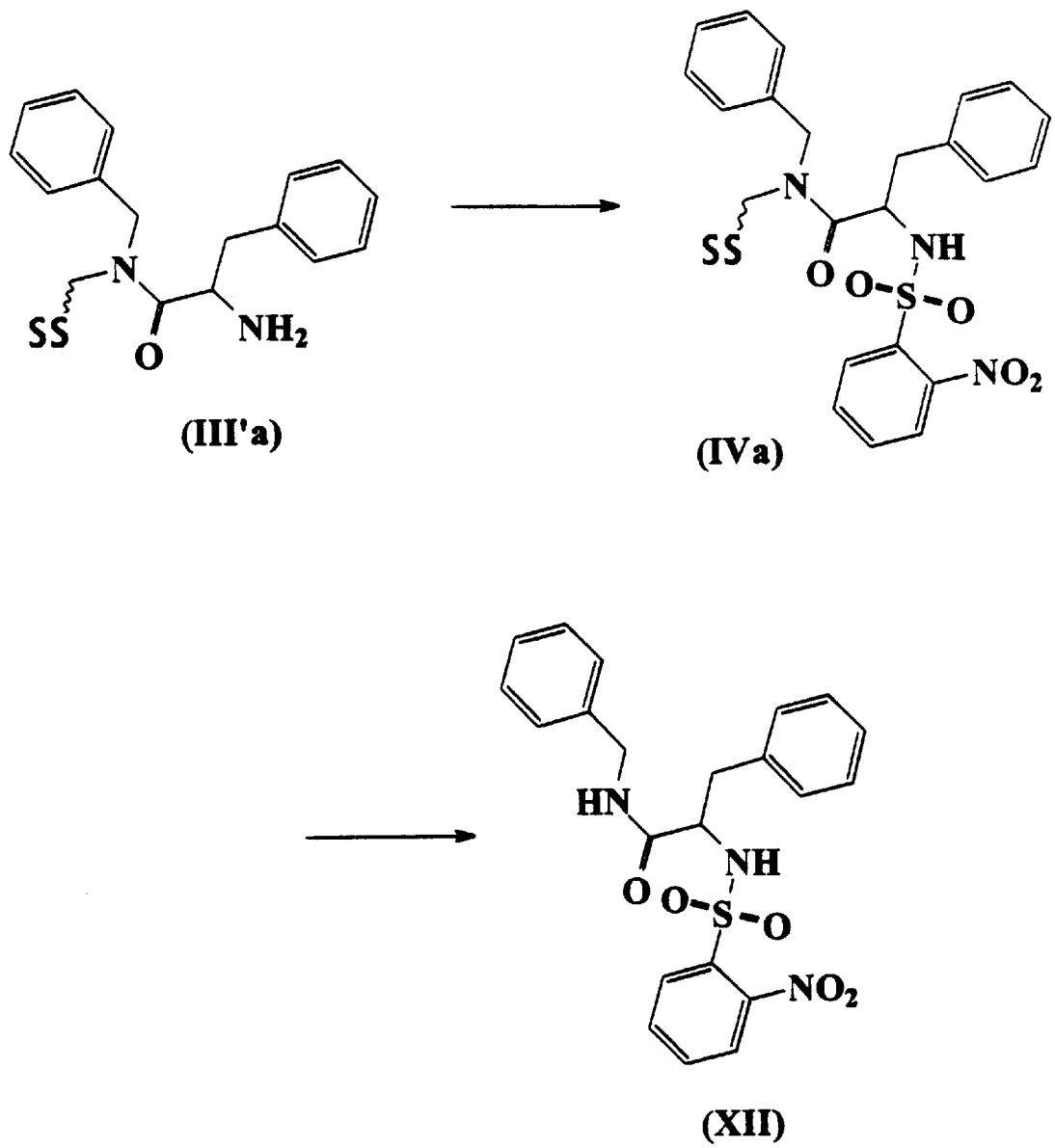
FIG. 5 shows a schematic for the synthesis of a sulfonyl protected amino acid derivative of an amide compound of formula (XII).
Figure 6:
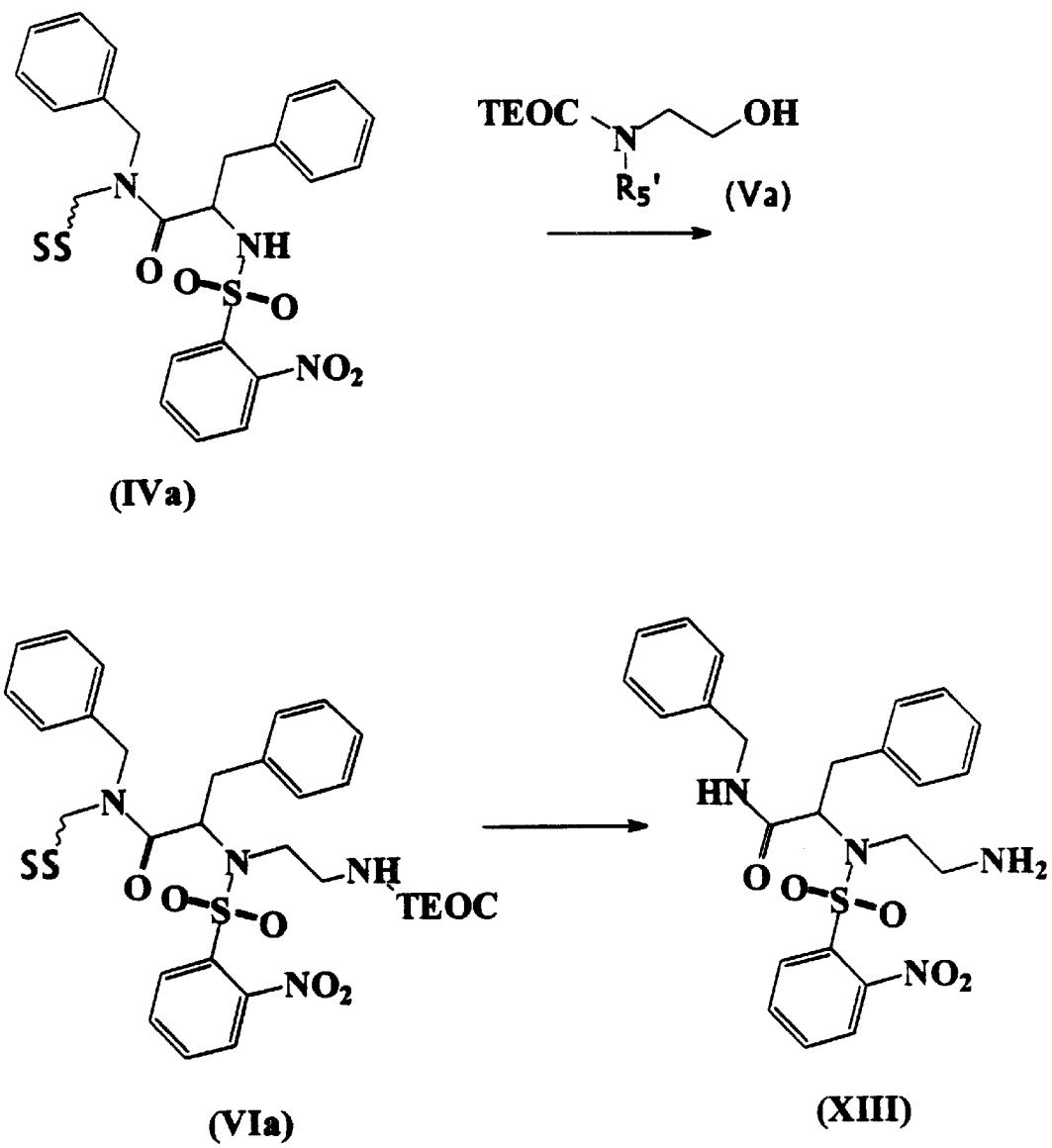
FIG. 6 shows a schematic for the synthesis of a sulfonyl protected amino acid derivative of an amide compound of formula (XIII).
Figure 7:
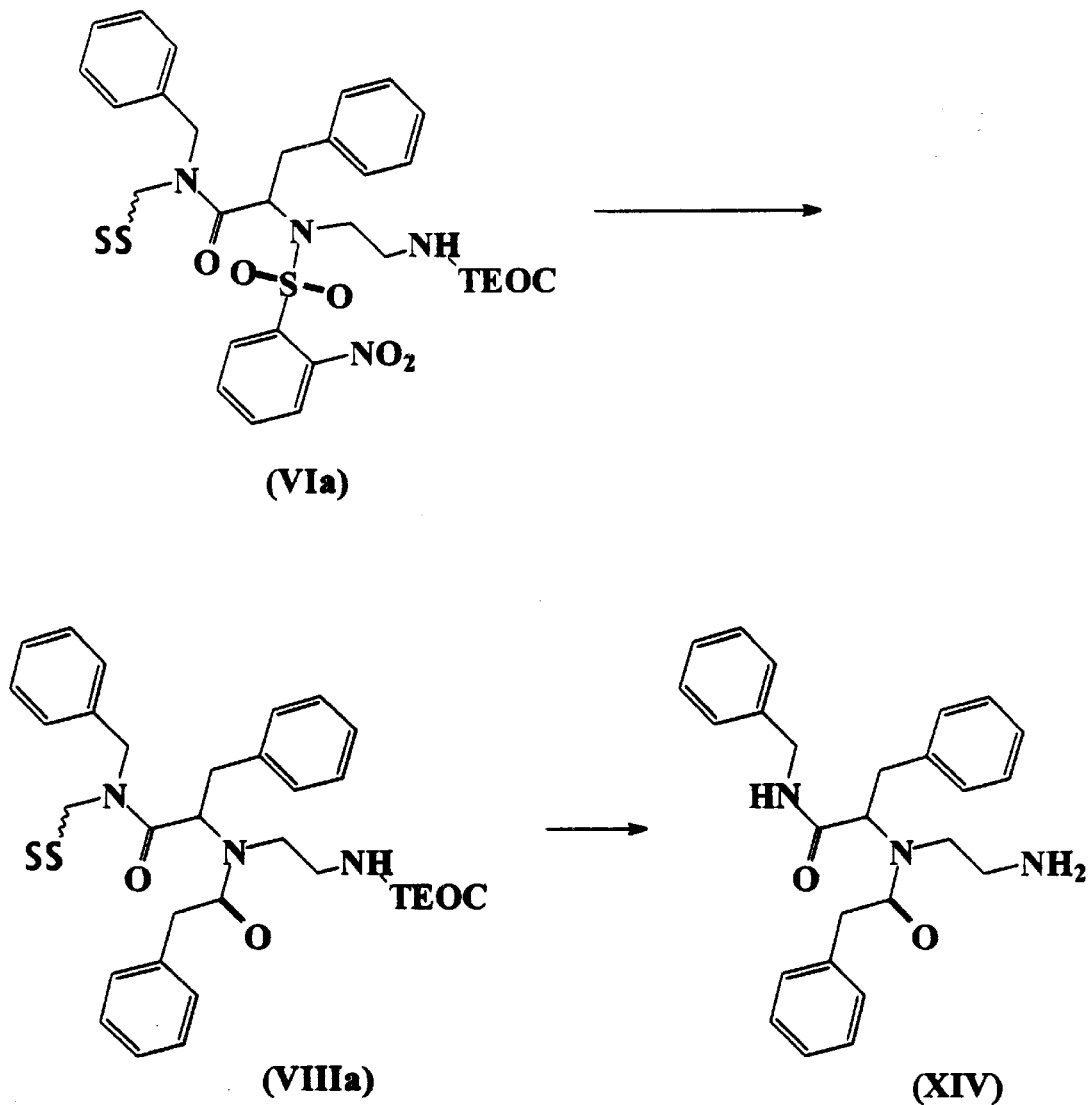
FIG. 7 shows a schematic for the synthesis of an amide compound of formula (XIV).
Figure 8:
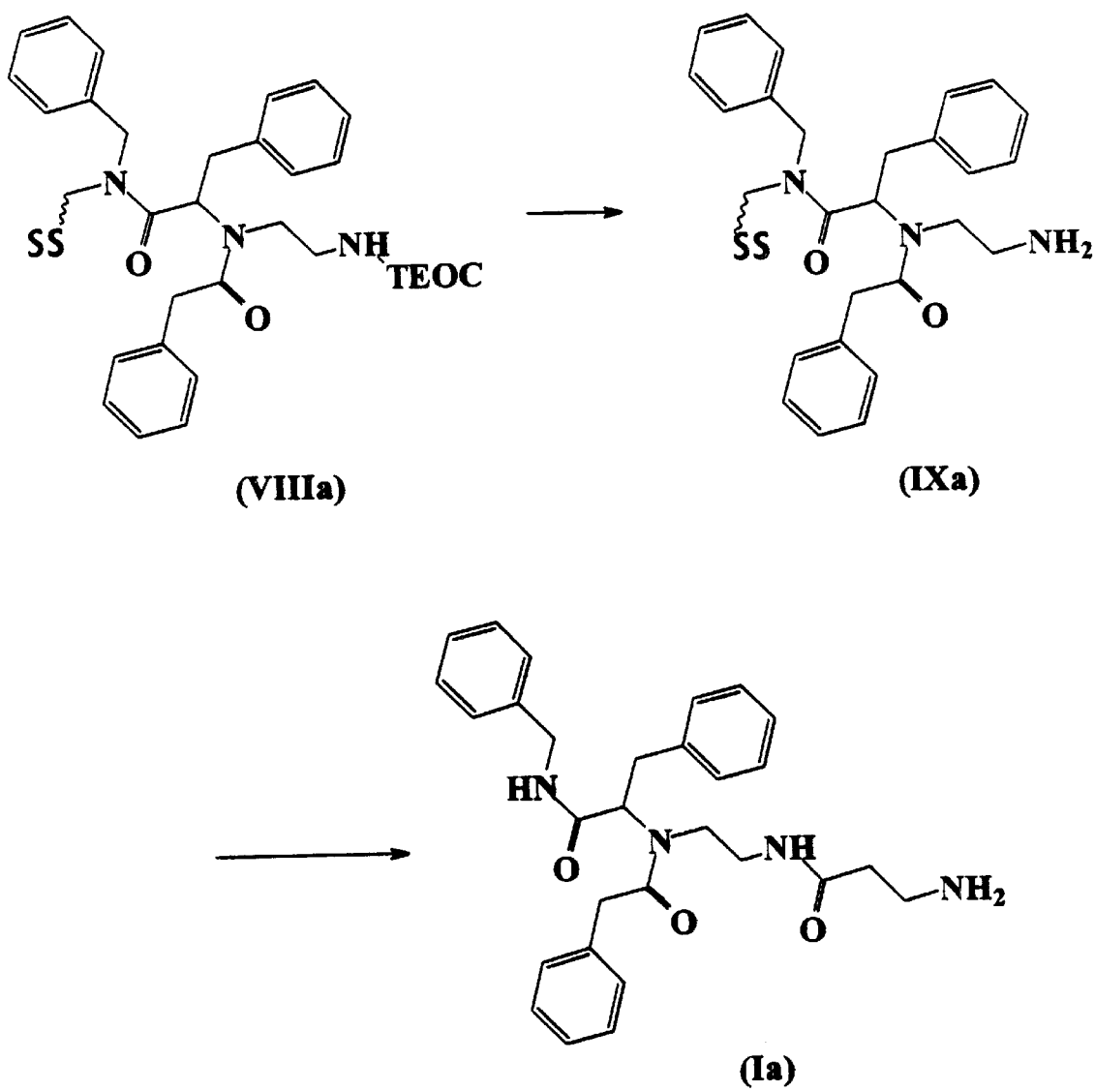
FIG. 8 shows a schematic for the synthesis of an amide compound of formula (Ia).

The present invention provides amide compounds of formula (I):

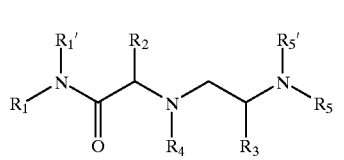
(I)

wherein:
each $R_1$, $R_{1'}$, $R_4$, $R_5$ and $R_{5'}$ is, independently, H, an amino protecting group, or $CH_2$, $CH(R_2)$, $C=O$, $C=S$, $S(=O)_2$, $C(=O)NH$, $C(=S)NH$ or $C(=O)O$ substituted with H or a hydrocarbyl group selected from $C_1$–$C_{10}$ alkyl, $C_2$–$C_{10}$ alkenyl, $C_2$–$C_{20}$ alkynyl, $C_6$–$C_{14}$ aryl, $C_6$–$C_{14}$ aralkyl, $C_3$–$C_{14}$ cycloalkyl, $C_5$–$C_{14}$ fused cycloalkyl, $C_4$–$C_{14}$ heterocycle, $C_4$–$C_{14}$ heterocyclylalkyl, $C_4$–$C_{14}$ heteroaryl, $C_4$–$C_{14}$ heteroarylalkyl or $CH(R_2)$—NH—$R_2$; wherein said hydrocarbyl group is optionally substituted with oxo, acyl, alkoxy, alkoxycarbonyl, alkyl, alkenyl, alkynyl, amino, amido, azido, aryl, heteroaryl, carboxylic acid, cyano, guanidino, halo, haloalkyl, haloalkoxy, hydrazino, hydroxyl, alkylsulfonyl, nitro, sulfide, sulfone, sulfonate, sulfonamide, thiol, and thioalkoxy, provided that $R_{1'}$ may also be a solid support and $R_4$ is not H; and each $R_2$ and $R_3$ is, independently, H or a hydrocarbyl group selected from $C_1$–$C_{10}$ alkyl, $C_2$–$C_{10}$ alkenyl, $C_2$–$C_{20}$ alkynyl, $C_6$–$C_{14}$ aryl, $C_6$–$C_{14}$ aralkyl, $C_3$–$C_{14}$ cycloalkyl, $C_5$–$C_{14}$ fused cycloalkyl, $C_4$–$C_{14}$ heterocyclyl, $C_4$–$C_{14}$ heterocycloalkyl, $C_4$–$C_{14}$ heteroaryl and $C_4$–$C_{14}$ heteroarylalkyl; wherein said hydrocarbyl group is optionally substituted with acyl, alkoxy, alkoxycarbonyl, alkyl, alkenyl, alkynyl, amino, amido, azido, aryl, heteroaryl, carboxylic acid, cyano, guanidino, halo, haloalkyl, haloalkoxy, hydrazino, hydroxyl, alkylsulfonyl, nitro, sulfide, sulfone, sulfonate, sulfonamide, thiol or thioalkoxy, provided that $R_2$ is not H.

The present invention also provides combinatorial libraries of amide compounds of formula (I).

The terms "library" and "libraries," as used herein, refers to a collection of compounds created by a combinatorial process having a common chemical structure or scaffold with one or more variable substituents, the scaffold in the present invention being an amide. Libraries include mixtures of compounds of the invention as well as individual compounds substantially free of other related compounds arranged in arrays. In a preferred embodiment, libraries of the invention comprise at least two, three, four or five compounds of formula (I). In another preferred embodiment, libraries of the invention comprises at least ten, fifteen, twenty, fifty or one hundred compounds of formula (I).

In preferred embodiments, each $R_1$, $R_4$, $R_5$ and $R_{5'}$ is, independently, hydrogen, an amino protecting group or a divalent group such as $CH_2$, $CH(R_2)$, $C=O$, $C=S$, $S(=O)_2$, $C(=O)NH$, $C(=S)NH$ or $C(=O)O$ substituted with H or a hydrocarbon chain such as $C_{1-10}$ alkyl, $C_{2-10}$ alkenyl or alkynyl, provided that $R_4$ is not hydrogen. The hydrocarbon chain is optionally substituted with a cyclic group such as a $C_{3-7}$ cycloalkyl, $C_{5-14}$ aryl, or 5-14-membered heterocycle or heteroaryl group. Included by the term "hydrocarbon chain" are straight and branched alkyl, alkenyl and alkynyl groups. By "hetero" is meant a group incorporating one or more heteroatom selected N, 0 and S as well as SO and $SO_2$. Said "cyclic group" may be mono-, bi- or tricyclic and may be substituted with substituents selected from halogen, hydroxyl, amino, carboxyl and alkyl.

Preferably, each $R_1$, $R_{1'}$, $R_4$, $R_5$ and $R_{5'}$ is selected from hydrogen, piperazinyl, benzyl, 1-(2-ethyl)imidazolidin-2-one, 2-pyridylmethyl, 1-(2-dimethylamino)ethyl, 2-(N-acetylamino)ethyl, thiophene-2-acetyl, 3-aminopropionyl, 6-quinolinecarboxyl, nicotinoyl, 2-pyrazine-carboxyl, carboxamidino, 3-(trifluoromethyl)benzoyl, carbamoyl, 2-aminopropionyl, imidazole-4-carboxyl, isonipecotyl, 3,5-diaminobenzoyl, isovaleryl, nalidixyl, 2-hydroxyacetyl, thymine-1-acetyl, aminocarbonyl, p-toluylsulfonyl, p-nitrophenylcarbonyl, p-toluylaminocarbonyl, 3,5-bis (trifluoromethyl)phenylcarbamoyl, 3-pyridylmethyl, di-t-butyl-, N-ethyl-3-carbazolylmethyl, anthraquinone-2-carbonyl, isobutyl, nalidixoyl, p-t-butyl-phenylcarbonyl, p-aminophenyl-carbonyl, cyclopropyl-carbonyl, 2-nitrophenyl-sulfonyl, (R)-(–)-2,2-dimethyl-5-oxo-1,3-dioxolane-4-acetyl, (S)-(+)-2,2-dimethyl-5-oxo-1,3-dioxolane-4-acetyl, carboxamidino, 2,6-dichloroisonicotinyl, carbamoylmethyl, 3-pyridylmethyl, 5-hydantoinacetyl, 2-amino-4-hydroxybutyryl, benzo[c]1,2, 5-oxadiazole-5-carboxyl, hydantoyl, niflumyl, orotyl and 2-phenylacetyl, provided that $R_{1'}$ may also be a solid support and $R_4$ is not hydrogen.

It is more preferred that $R_1$ be selected from benzyl, (2-aminoethyl)dimethyl, 1-(2-ethyl)-imidazolidin-2-one, 2-pyridylmethyl, 1- (2-dimethylamino)ethyl and 2-(N-acetylamino)ethyl.

It is further preferred that $R_4$ be selected from isonipecotyl, isobutyl, 3-pyridylmethyl, 3,5-bis-(trifluoromethyl)benzyl, hydantoyl, (2S)-2-amino-3-hydroxypropionyl, nalidixoyl, 3-pyridylacetyl, thymine-1-acetyl, cytosine-1-acetyl, adenine-9-acetyl, guanine-9-acetyl thiophene-2-acetyl, hydroxyacetyl, 3-aminopropionyl and 6-quinolinecarboxyl.

It is still further preferred that $R_5$ and $R_{5'}$ be selected from imidazole-4-carboxyl, hydroxyacetyl, nicotinoyl and 3-aminopropionyl.

It is more preferred that $R_5$ be selected from hydrogen, (R)-(–)-2,2-dimethyl-5-oxo-1,3-dioxolane-4-acetyl, (2S)-2-amino-4-hydroxybutyryl, isonipecotyl, 3,5-diaminobenzoyl, (2S,3R)-2-amino-3-hydroxybutyryl, carbamoyl, carboxamidino, 1-fluorenecarboxyl, orotyl, nalidixoyl, 6-quinolinecarboxyl, thymine-1-acetyl, cytosine-1-acetyl, adenine-9-acetyl, guanine-9-acetyl, 3-(carbamoyl)benzoyl imidazole-4-carboxyl, hydroxyacetyl, nicotinoyl and 3-aminopropionyl.

In another preferred embodiment, substituents $R_2$ and $R_3$ are selected independently from hydrogen or a hydrocarbon chain such as $C_{1-10}$ alkyl, $C_{2-10}$ alkenyl or alkynyl, the chain being optionally substituted with a cyclic group such as a $C_{3-7}$ cycloalkyl, $C_{5-14}$ aryl, or 5-14 membered heterocycle or heteroaryl group, provided that $R_2$ is not hydrogen. The terms "hydrocarbon chain," "hetero" and "cyclic group" are as defined above.

It is more preferred that $R_2$ be selected from methyl, isobutyl, benzyl, 1-hydroxyethyl, carboxymethyl, aminomethyl, carbamoylmethyl, 2-carbamoylethyl, 3-(amidinoamino)propyl, 4-aminobenzyl, 2-aminomethyl, 3-indolylmethyl, imidazol-4-ylmethyl, hydroxymethyl, 4-aminobutyl, 2-carboxyethyl and 4-hydroxybenzyl.

It is also preferred that $R_3$ be selected from hydrogen, hydroxymethyl, methyl, isobutyl, benzyl, 1-hydroxyethyl, 2-carboxyethyl, carboxymethyl, aminomethyl, 4-hydroxybenzyl, carbamoylmethyl, 2-carbamoylethyl, 3-(amidinoamino)propyl, 4-aminobenzyl, 2-aminoethyl, 3-indolylmethyl and imidazol-4-ylmethyl.

It is preferred that $R_{1'}$ be hydrogen or a solid support. Solid supports, also called resins, according to the present invention, include controlled pore glass (CPG), polystyrene and cross-linked polystyrene/divinylbenzene resins, polyethylene glycol grafted polymers such as polystyrene, tentagel(R), Argogel(R), or Poros (a copolymer of polystyrene/divinylbenzene). These may be functionalized with a variety of groups including, but not limited to, hydroxy, carboxy, thio, amino, and aldehyde, for example, Wang resin, Merrifield resin, hydroxymethyl polystyrene resin, formyl polystyrene resin, aminomethyl (AM) resin, MBHA resin, Rink amide and acid resins, Seiber resin, oxime resin, trityl resin, and thiol 4-methoxytrityl resin. Particularly useful are solid supports bearing aldehyde linkers that allow for loading of amine compounds to form amide scaffolds of this invention via reductive amination reactions. A number of commercially available supports, such as ArgoGel-MB-CHO resin, bear pendant aldehyde linkers that may be used for this purpose. Alternatively, acid-stable resins including, but not limited to, ArgoGel-OH may be derivatized with linkers such as, but not limited to, hydroxybenzaldehydes via Mitsunobu reactions so as to generate a pendant phenoxybenzaldehyde that is subsequently used for reaction with an amine compound.

It will be appreciated that compounds of the present invention incorporate chiral centers and, therefore, exist as geometric isomers and stereoisomers. All such isomers are contemplated and are within the scope of the invention whether in pure isomeric form or in mixtures of such isomers as well as racemates.

"Amino protecting groups" are used to block reactive amino sites or amino combinatorial sites on the scaffold. Once the scaffold is synthesized on the solid support, the amino-protecting group can be removed under basic (non-hydrolytic) conditions. The amino group is then derivatized, or functionalized, with the diverse building block or functional group of choice. This building block can be attached to the amino combinatorial site via a variety of linkages including, but not limited to, alkyl, amide, sulfonamide, carbamate, urea, aminoalkane, thiocarbamate, and thiourea. This can be accomplished by choosing the appropriate electrophile to functionalize the amino group. For example, carboxylic acids can be activated using peptide coupling reagents such as EDC, BOP or HATU and reacted with the scaffold nitrogen atom to give amides. Other reagents which can be used include, among others, acid chlorides, acid fluorides, acid imidazolides, acid anhydrides, sulfonyl chlorides, chloroformates, isocyanates, aldehydes (under reductive alkylation conditions), alkyl halides, and isothiocyanates. Thus, each time a specific linkage is desired in a library, it is introduced onto the scaffold via the appropriate coupling conditions using suitable building blocks at the amino combinatorial site.

Another feature of the present invention is the introduction of additional sites of diversity onto the scaffolds of the present invention. This may be accomplished via the use of functionalized building blocks for reaction at the amino combinatorial sites. Such building blocks include, among others, Fmoc-amino acids where the amino group of the amino acid building block is selectively protected with a labile protecting group, such as Fmoc. The carboxylic group of the amino acid building block reacts with the amino combinatorial site on the scaffolds of this invention. The products so generated may be further combinatorialized via deprotection of the Fmoc group on the pendant amino group derived from the previously used amino acid building block and reaction of this amine with additional building blocks as described below. Monocyclic, bicyclic and oligomeric amide libraries of this invention may therefore bear two or more sites of diversity based on the selective protection and deprotection of functional groups including amines and alcohols on the scaffolds and based on the building blocks used.

Amino-protecting groups stable to acid treatment are selectively removed with base treatment, and are used to make reactive amino groups selectively available for substitution. Examples of such groups are the FMOC (E. Atherton and R. C. Sheppard in The Peptides, S. Udenfriend, J. Meienhofer, Eds., Academic Press, Orlando, 1987, volume 9, p.1), and various substituted sulfonylethyl carbamates exemplified by the Nsc group (Samukov et al., *Tetrahedron Lett*, 1994, 35:7821; Verhart and Tesser, *Rec. Trav. Chim. Pays-Bas*, 1987, 107:621). Additional amino-protecting groups include but are not limited to, carbamate-protecting groups, such as 2-trimethylsilylethoxycarbonyl (Teoc), 1-methyl-1-(4-biphenylyl)ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide-protecting groups, such as formyl, acetyl, trihaloacetyl, benzoyl, and nitrophenylacetyl; sulfonamide-protecting groups, such as 2-nitrobenzenesulfonyl; and imine- and cyclic imide-protecting groups, such as phthalimido and dithiasuccinoyl. Equivalents of these amino-protecting groups are also encompassed by the compounds and methods of the present invention. Therefore, although the some of the compounds and methods of the present invention depict FMOC and 2-nitrobenzylsulfonyl protecting groups, equivalents of these groups are also encompassed by the compounds and methods of the present invention. The art-skilled are familiar with such equivalent amino-protecting groups. As an example, which is not intended to be limiting, amino protecting groups such as 2,6-dinitrobenzenesulfonyl, 4-nitrobenzenesulfonyl or 2,4-dinitrobenzenesulfonyl groups may be used. Alternatively, another amino protecting may be used instead of a sulfonyl protecting group.

In a particular aspect of the invention there are provided methods for preparing compounds of formula (I). comprising:

(a) attaching an amine to a solid support to form a solid support-bound amine of formula (II) wherein SS is a solid support;

(b) reacting compound (II) with an FMOC-protected amino acid to form an amide compound of formula (III);

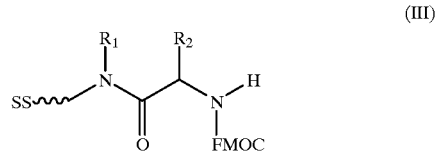

(c) replacing the FMOC protecting group on the amino acid with an amino protecting group to form an amide compound of formula (IV) wherein Ag is an amino protecting group;

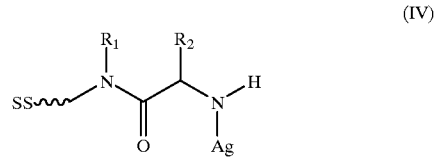

(d) reacting the secondary amine moiety of the compound of formula (IV) with a protected aminohydroxy compound of formula (V) wherein Pg is a protecting group;

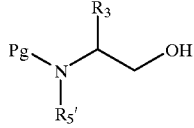
(V)

to form an amide compound of formula (VI);

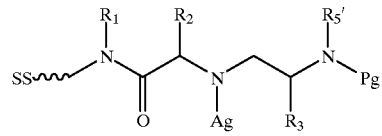
(VI)

(e) removing the amino protecting group of the compound of formula (VI) to form an amide compound of formula (VII) bearing a protected terminal primary amine moiety and a secondary amine moiety;

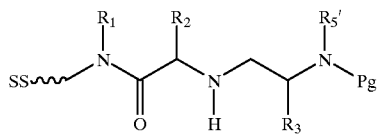
(VII)

(f) reacting the secondary amine of the compound of formula (VII) with an $R_4$ building block to form an amide compound of formula (VIII) bearing a protected terminal primary amine moiety;

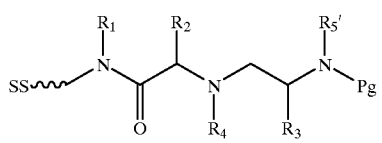
(VIII)

(g) removing the protecting group on the terminal primary amine moiety to form an amide compound of formula (IX); and

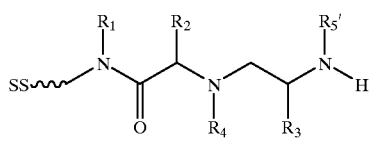
(IX)

(h) reacting the deprotected primary amine moiety with an $R_5$ building block to form an amide compound of formula (X).

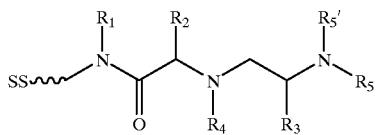
(X)

Also provided, in accordance with the present invention, are methods further comprising cleaving amide compounds of formula (X) from the solid support to form amide compounds of formula (I).

The present invention further provides methods for the preparation of compounds of formula (XV):

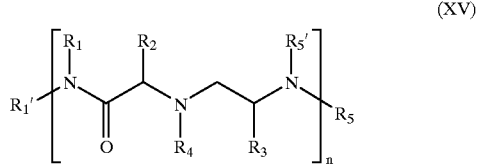
(XV)

wherein:

each $R_1$, $R_{1'}$, $R_4$, $R_5$ and $R_{5'}$ is, independently, H, an amino protecting group, or $CH_2$, $CH(R_2)$, $C=O$, $C=S$, $S(=O)_2$, $C(=O)NH$, $C(=S)NH$ or $C(=O)O$ substituted with H or a hydrocarbyl group selected from $C_1$–$C_{10}$ alkyl, $C_2$–$C_{10}$ alkenyl, $C_2$–$C_{20}$ alkynyl, $C_6$–$C_{14}$ aryl, $C_6$–$C_{14}$ aralkyl, $C_3$–$C_{14}$ cycloalkyl, $C_5$–$C_{14}$ fused cycloalkyl, $C_4$–$C_{14}$ heterocycle, $C_4$–$C_{14}$ heterocyclylalkyl, $C_4$–$C_{14}$ heteroaryl, $C_4$–$C_{14}$ heteroarylalkyl or $CH(R_2)$—NH—$R_2$; wherein said hydrocarbyl group is optionally substituted with oxo, acyl, alkoxy, alkoxycarbonyl, alkyl, alkenyl, alkynyl, amino, amido, azido, aryl, heteroaryl, carboxylic acid, cyano, guanidino, halo, haloalkyl, haloalkoxy, hydrazino, hydroxyl, alkylsulfonyl, nitro, sulfide, sulfone, sulfonate, sulfonamide, thiol, and thioalkoxy, provided that $R_{1'}$ may also be a solid support and $R_4$ is not H;

each $R_2$ and $R_3$ is, independently, H or a hydrocarbyl group selected from $C_1$–$C_{10}$ alkyl, $C_2$–$C_{10}$ alkenyl, $C_2$–$C_{20}$ alkynyl, $C_6$–$C_{14}$ aryl, $C_6$–$C_{14}$ aralkyl, $C_3$–$C_{14}$ cycloalkyl, $C_5$–$C_{14}$ fused cycloalkyl, $C_4$–$C_{14}$ heterocyclyl, $C_4$–$C_{14}$ heterocycloalkyl, $C_4$–$C_{14}$ heteroaryl and $C_4$–$C_{14}$ heteroarylalkyl; wherein said hydrocarbyl group is optionally substituted with acyl, alkoxy, alkoxycarbonyl, alkyl, alkenyl, alkynyl, amino, amido, azido, aryl, heteroaryl, carboxylic acid, cyano, guanidino, halo, haloalkyl, haloalkoxy, hydrazino, hydroxyl, alkylsulfonyl, nitro, sulfide, sulfone, sulfonate, sulfonamide, thiol or thioalkoxy; and n is 1 to 25; comprising the steps of:
(a) attaching an amine to a solid support to form a solid support-bound amine of formula (XVI) wherein SS is a solid support;

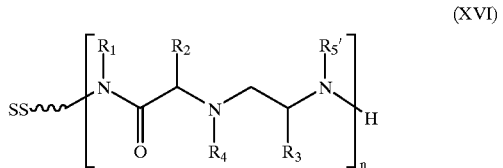
(XVI)

(b) reacting compound (XVI) with an FMOC-protected amino acid to form an amide compound of formula (XVII);

(XVII)
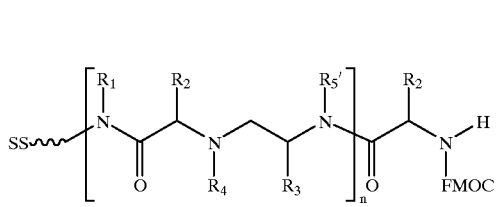

(c) replacing the FMOC protecting group on the amino acid with an amino protecting group to form an amide compound of formula (XVIII) wherein Ag is an amino protecting group;

(XVIII)
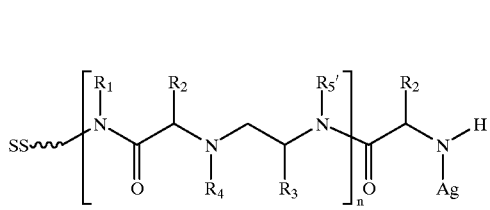

(d) reacting the secondary amine moiety of the compound of formula (XVIII) with a protected aminohydroxy compound of formula (V) wherein Pg is a protecting group;

(V)
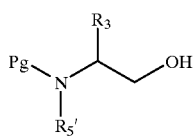

to form an amide compound of formula (XIX);

(XIX)
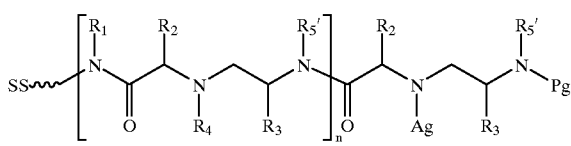

(e) removing the amino protecting group of the compound of formula (XIX) to form an amide compound of formula (XX) bearing a protected terminal primary amine moiety and a secondary amine moiety;

(XX)
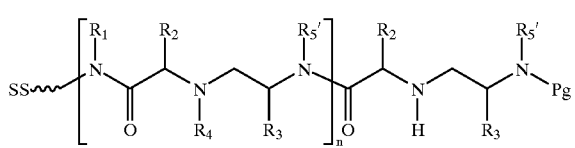

(f) reacting the secondary amine of the compound of formula (XX) with an $R_4$ building block to form an amide compound of formula (XXI) bearing a protected terminal primary amine moiety;

(XXI)
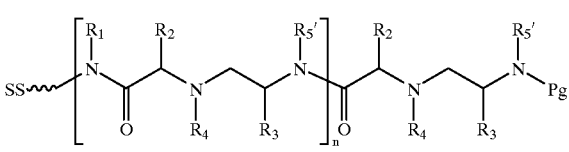

(g) removing the protecting group on the terminal primary amine moiety to form an amide compound of formula (XXII); and (XXII)
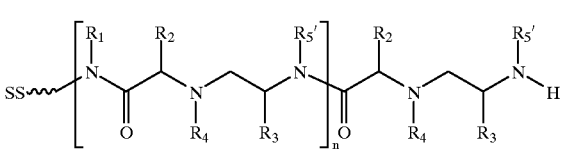

(h) reacting the deprotected primary amine moiety with an $R_5$ building block to form an amide compound of formula (XXIII).

(XXIII)
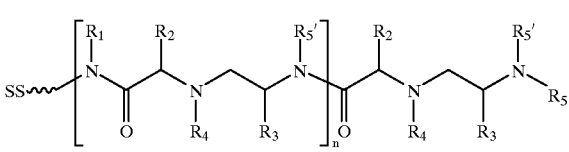

Also provided, in accordance with the present invention, are methods further comprising cleaving amide compounds of formula (XXIII) from the solid support to form amide compounds of formula (XV).

Compounds of formula (XVI) may be synthesized by procedures known in the art. Such procedures are described in U.S. Pat. No. 5,539,083, issued Jul. 23, 1996; U.S. Pat. No. 5,831,014, issued Nov. 3, 1998; U.S. application Ser. No. 08/466,395, filed Jun. 6, 1995; and U.S. application Ser. No. 09/131,270, filed Aug. 7, 1998. The entire contents of the aforementioned patents and applications are commonly assigned and herein incorporated by reference in their entirety.

By "building block" is meant a reagent for synthesizing, derivatizing or functionalizing the amide compound or scaffold of the present invention. Suitable building blocks include sulfonyl halides, triphosgene, isocyanates, isothiocyanates, acid halides, carboxylic acids, aryl halides, alkyl halides, aldehydes, ketones and activated guanylating agents.

It is preferred that $R_1$, $R_4$, $R_5$ and $R_{5'}$ building blocks be selected from carboxylic acids, acid halides, sulfonyl halides, isocyanates, aldehydes, ketones, alkyl halides, aryl halides and activating guanylating agents, and $R_1$, be hydrogen or a solid support.

Preferred $R_1$, $R_4$, $R_5$ and $R_{5'}$ building blocks are selected from 2-pyrazinecarboxylic acid, 3,5-bis (trifluoromethyl) phenyl isocyanate, 3-(trifluoromethyl)benzoic, acid, 4-methoxybenzyl isocyanate, BOC-beta-ALA-OH, BOC-imidazole-4-carboxylic acid, BOC-isonipecotic acid, bis (BOC-3,5-diaminobenzoic acid), isovaleric acid, nalidixic acid, t-butoxyacetic acid, thymine-1-acetic acid, 3-pyridinecarboxaldehyde, di-tert-butyl dicarbonate, N-ethyl-3-carbazolecarboxaldehyde, anthraquinone-2-carboxylic acid, isobutyraldehyde, (R)-(–)-2,2-dimethyl-5-oxo-1,3-dioxolane-4-acetic acid, (S)-(+)-2,2-dimethyl-5-oxo-1,3-dioxolane-4-acetic acid, 1H-pyrazole-1-carboxamidine-HCl, 2,6-dichloroisonicotinic acid, 2-bromoacetamide, 3-pyridinecarboxaldehyde, 5-hydantoinacetic acid, N-BOC-L-homoserine, benzofurazan-5-carboxylic acid, hydantoic acid, niflumic acid and orotic acid.

It is more preferred that $R_4$ building blocks be selected from thiophene-2-acetic acid, t-butoxyacetic acid, BOC-β-Ala-OH and 6-quinoline carboxylic acid. It is more preferred that $R_5$ and $R_{5'}$ building blocks be selected from BOC-imidazole-4-carboxylic acid, t-butoxyacetic acid, nicotinic acid and BOC-β-Ala-OH.

It is further preferred that $R_2$ building blocks be selected from N-FMOC-O-t-butyl-L-serine, N-FMOC-L-Lys(BOC)-OH, N-FMOC-Glu(O-t-Bu)-OH and N-FMOC-O-t-Bu-L-Tyr. A preferred $R_3$ building block is N-TEOC-ethanolamine.

The methods for preparing amide compounds of the present invention may be carried out in any vessel capable of holding the liquid reaction medium. In one embodiment, the process of the invention is carried out in containers adaptable to parallel array synthesis. In particular, the amide combinatorial library of the present invention can be formed in a 96-well plate, and typically in a two-dimensional array of defined reservoirs, wherein an amide compound of formula (I) is prepared in each reservoir. Thus the library comprises a plurality of reservoir arrays, e.g. well plates, each well containing a discrete compound or mixture of compounds. Following simultaneous preparation of the library compounds in the array, the compounds can be transferred, in whole or in part, to other reservoir arrays to prepare multiple copies of the library apparatus, or to subject the library to additional reactions or biological assays. Copies of the library apparatus (daughter well plates, each comprising a 2-dimensional array of defined reservoirs with each reservoir containing a predetermined reaction product of the library) are useful as replaceable elements in automated assay machines. The apparatus allows convenient access to a wide variety of amide compounds of the present invention. A preferred reservoir array for use in making the library is a multi-well titer plate, typically a 96-well microtiter plate. Upon completion, reaction products may be analyzed by mass spectrometry and nuclear magnetic resonance spectrometry.

In one aspect of the present invention, there are provided assay kits for the identification of pharmaceutical lead compounds. The assay kit comprises a well plate apparatus containing an array of amide compounds of the present invention (discrete compounds or mixtures thereof) and biological assay materials. The biological assay materials employed will be those predictive of success for an associated disease state. Illustrative biological materials useful in the kit of the present invention are those required to perform the following assays:

enzymatic inhibition
receptor-ligand binding
protein-protein interaction
protein-DNA interaction
cell-based functional assays
transcriptional regulation
signal transduction/second messenger
viral infectivity
incubate and read assays
scintillation proximity assays
angiotensin II IPA receptor bidning assay
endothelia convertin enzym $^{125}$I SPA assay
HIV proteinase $^{125}$I SPA enzyme assay
cholesteryl ester transfer (CETP) $^3$H SPA assay
fluorescence correlation spectroscopy
colorimeric biosensors
$Ca^{2+}$ EGTA for cell-based assays
receptor gene constructs for cell-based assays
lucerferase, green fluorescent protein, beta-lactamase
electrical cell impedance sensor assays.

EXAMPLES

HPLC was performed with a Waters 625 LC pump and 717 autosampler, equipped with a Waters 996 diode-array UV-Vis detector and a SEDEX S.E.D.E.R.E Model 55 Evaporative Light Scattering (ELS) detector. The column used was a Phenomenex Luna C8, 3 uM particle, 4.6×100 mm. A typical elution profile is 100% 0.1% (v/v) TFA in water in a linear gradient to 100% 0.1% TFA in acetonitrile over 10 minutes.

Mass spectra were recorded using a Hewlett-Packard model MSD 1100 LCMS. Spectra were recorded in positive mode using either atmospheric-pressure chemical ionization (APCI) or atmospheric-pressure electrospray ionization methods. Thin layer chromatography (TLC) was performed using EM Sciences plates (5534-3), eluted with 10% methanol in $CH_2Cl_2$, and visualized by treating with 10% phosphomolybdic acid in ethanol and heating with a heat gun.

Nuclear Magnetic Resonance (NMR) were collected on a Varian Gemini 200. Gel-phase $^{13}$C NMR were collected on a Bruker AM 400 spectrophotometer.

Example 1

Preparation of benzylamino-derivatized resin 2-methoxy-4-alkoxy-benzaldehyde ArgoGel-MB-CHO™ (SS, MB-CHO-ArgoGel, 10 g, 0.4 mmole/g) was swelled in 50 ml $CH_2Cl_2$ and filtered, washed with 50 ml dry MeOH, filtered, and slurried in 30 ml dry trimethylorthoformate (TMOF). Benzylamine (0.52 ml, 4.8 mmole) was added and the slurry swirled gently on a shaker table under dry nitrogen overnight. A solution of 40 ml dry methanol, acetic acid (0.46 ml, 8.0 mmole) and borane-pyridine complex (1.0 ml, 8.0 mmole) was added, and the slurry swirled overnight. The resin was filtered, and washed several times with methanol, DMF, $CH_2Cl_2$, and finally methanol. Gel-phase NMR showed complete conversion from the aldehyde to secondary benzylamine derivative (IIa). Gel-phase $^{13}$C NMR ($C_6D_6$) δ 40.9, 48.1, 53.0, 54.8, 67.7, 70.9 (PEG linker), 99.5, 104.7, 121.3, 127.0, 127.8 (poly-styrene beads), 128.5, 130.5, 141.2, 159.0, 159.8.

The supports (IIb)–(IIf) were similarly prepared from the corresponding amines. Support (IIg) was prepared by treating ArgoGel-Wang™ support with 3.5 eq. of carbonyldiimidazole in acetonitrile overnight, then washing with dry acetonitrile (3×), then treating with 1 M piperazine in DMF for 1 h, followed by washing with DMF (3×), $CH_2Cl_2$ (3×), and MeOH (3×).

Example 2

Preparation of protected Fmoc-amino acid derivative of Example 1

250 mg of benzylamine resin (IIa) was swelled in $CH_2Cl_2$, washed several times with dry $CH_2Cl_2$ followed by dry DMF under an inert atmosphere. The resin was treated with the HATU active ester of Fmoc-L-phenylalanine created in situ from a mixture of 0.2 M Fmoc-L-phenylalanine, 0.2 M HATU and 0.6 M 2,4,6-collidine in DMF. The slurry was gently agitated on a shaker plate for 3 hours, after which the resin (IIIa) was flushed with nitrogen, and washed with DMF (3×) and $CH_2Cl_2$ (3×). The resin was then treated with 0.5 ml of 10% (v/v) piperidine in DMF for 10 minutes to remove the Fmoc group. This treatment was repeated, then the resin was washed with DMF (3×), $CH_2Cl_2$ (3×), and again with DMF (3×), to give resin (III'a).

Half of the resin was removed and treated with 0.5 ml 95/5 (v/v) trifluoracetic acid (TFA)/triisopropylsilane (TIS) for four hours to cleave the desired product (XI) from the resin. The eluent was filtered, dried, weighed, and subjected to HPLC and mass spectral (MS) analysis. Mass yield 13.0 mg, 100%. HPLC shows 93% purity, and the main ion in the mass spectrum was the expected M+H=255.1.

Example 3

Preparation of 2-nitrobenzenesulfonyl derivative of Example 2

Resin (III'a) from Example 2 was treated with 0.5 ml of a solution of 0.2 M 2-nitrobenzenesulfonyl chloride, 0.2 M N,N-diisopropylamine (DIPEA) in $CH_2Cl_2$ and agitated gently for 1 hour. The solution was flushed, and the resin (IVa) washed with $CH_2Cl_2$ (3×) and DMF (3×).

A small portion of the resin was removed and treated with 0.5 ml of 95/5 (v/v) TFA/ethanedithiol (EDT) for 4 hours. The eluent was filtered, dried, reconstituted in acetonitrile, and subjected to HPLC and MS analysis. HPLC shows 99% purity, and the main ion in the mass spectrum (APCI) was the expected M+H=438.1 for (XII).

Example 4

Alkylation of 2-nosylamide amino acid derivative

Resin (IVa) from Example 3 was treated with 0.25 ml of 0.4 M N-Teoc-ethanolamine (Va) from Example 7, and 0.4 M triphenylphosphine (TPP) in $CH_2Cl_2$. 0.4 M N,N'-diisopropylazodicarboxylate (DIAD) in $CH_2Cl_2$ was added dropwise over several minutes with swirling of the resin slurry. The slurry was agitated gently for 2 hours under inert atmosphere. The solution was flushed, and the resin (VIa) was washed with $CH_2Cl_2$ (3×), DMF (3×) and again with $CH_2Cl_2$ (3×).

A small portion of the resin was removed and treated with 0.5 ml of 95/5 (v/v) TFA/ethanedithiol (EDT) for 4 hours. The eluent was filtered, dried, reconstituted in acetonitrile, and subjected to HPLC and MS analysis. HPLC shows 94% purity, and the main ion in the mass spectrum was the expected M+H=482.1 for (XIII).
Note: The Teoc group was removed by the TFA treatment.

Example 5

Derivatization of Teoc-aminoethyl amino acid derivative

Resin (VIa) from Example 4 was treated with a 0.5 ml 0.5 M mercaptoacetic acid, 1.0 M 1,8-diazabicyclo-[5.4.0]undec-7-ene (DBU) in DMF for 1 hour to remove the 2-nosyl group. The resin was washed with DMF (3×), $CH_2Cl_2$ (3×), methanol (3×), and again with $CH_2Cl_2$ (3×) and DMF (3×).

The resin was then treated with the HATU active ester of phenylacetic acid created in situ from a mixture of 0.2 M phenylacetic acid, 0.2 M HATU and 0.6 M 2,4,6-collidine in DMF. The slurry was gently agitated on a shaker plate for 3 hours, after which the resin (VIIIa) was flushed with nitrogen, and washed with DMF (3×) and $CH_2Cl_2$ (3×).

A small portion of the resin was removed and treated with 0.5 ml 95/5 (v/v) TFA/TIS for four hours to cleave the desired product (XIV) from the resin. The eluent was filtered, dried, and subjected to HPLC and mass spectral (MS) analysis. HPLC shows 85% purity, and the main ion in the mass spectrum was the expected M+H=416.2.

Note: Derivatives of (XIV) that have not been acylated are not stable to the TFA cleavage step, so cannot be isolated.

Example 6

Derivatization of aminoethyl amino acid derivative

Resin (VIIIa) from Example 5 was treated with 0.5 ml of 0.3 M tetrabutylammonium fluoride hydrate (TBAF) in N-methylpyrrolidinone for 2 hours to remove the Teoc group. The resin was flushed and washed with DMF (3×), methanol (3×), $CH_2Cl_2$ (3×) and DMF (3×).

The resulting resin (IXa) was then treated with the HATU active ester of (N-(t-butyloxycarbonyl)) β-alanine (Boc-β-alanine) created in situ from a mixture of 0.2 M Boc-β-alanine, 0.2 M HATU and 0.6 M 2,4,6-collidine in DMF. The slurry was gently agitated on a shaker plate for 1 hour, after which the resin was flushed with nitrogen, and washed with DMF (3×), $CH_2Cl_2$ (3×), methanol (3×), and again with $CH_2Cl_2$ (3×)

The resin was then treated with 0.5 ml 95/5 (v/v) TFA/TIS for four hours to cleave the desired product (Ia) from the resin. The eluent was filtered, dried, and subjected to HPLC and mass spectral (MS) analysis. HPLC shows 81% purity, and the main ion in the mass spectrum was the expected M+H=487.2.

Example 7

Preparation of (N-Teoc)ethanolamine (Va)

Teoc-N-hydroxysuccinamide (100 g, 386 mmole) was dissolved in 200 ml dioxane with stirring and gentle heating, then the cloudy solution was transferred to a 500 ml addition funnel. A second solution of ethanolamine (48.8 ml, 808 mmole, 2.1 eq.) dissolved in 250 ml 3:2 water:dioxane in a 1000 ml round-bottom flask was cooled to 0° C. with an ice-water bath. The Teoc-N-hydroxysuccinamide solution was added dropwise to the ethanolamine solution over 30 minutes. The slurry was stirred and allowed to warm to room temperature. After 2 hours the slurry was evaporated to a sludge on a rotary evaporator. 200 ml of acetonitrile was added and again the slurry was reduced under vacuum to a sludge. The material was dried overnight in vacuo. The next day the material was extracted with 3 volumes of 200 ml ethyl acetate, and the extract was applied to the top of a column of silica gel packed in ethyl acetate. The column was eluted with 2 liters ethyl acetate, and the appropriate fractions were evaporated to a clear oil on the rotary evaporator. Residual water was removed by adding 200 ml acetonitrile and evaporating. Isolated yield was 68.95 g (85%). $^1$H NMR ($CDCl_3$) δ-0.03 (s, 9H), 0.88–0.97 (m, 2H), 3.22–3.29 (m, 2H), 3.48 (OH, 1H), 3.60–3.65 (t, 2H), 4.05–4.13 (m, 2H) 5.45 (NH, 1H). $^{13}$C NMR ($CDCl_3$) δ-1.5, 17.74, 43.4, 62.2, 63.3, 157.7. Any substituted ethanolamine can be utilized in this procedure. Many of these are commercially available derivatives of amino-acids.

Example 8

Automated synthesis of library compounds

A resin or resin mixture of general formula (II) is prepared manually in bulk, then loaded into a 96-well reaction vessel and loaded onto a parallel array synthesizer described in Brennan et. al. *Biotechnol. Bioeng*. 1998, 61/1, 33–45. The synthesizer is then loaded with the following command file input (saved as a tab-delimited text file):

```
INITIAL_WASH
        BEGIN
                Repeat          4
                                Add DCM 300
                                Drain 15
                End_Repeat
                Repeat          4
                                Add DMF 300
                                Drain 25
                End_Repeat
        END
R2_FUNCTIONALIZATION
        BEGIN
                Next_Sequence
                Repeat          3
                set             0.08
                wait            15
                prime           <SEQ>
                prime           <ACT1>
                                Add <SEQ> 200
                                Wait 3600
                                Drain 15
                End_Repeat
                Nozzle_Wash     <SEQ>
                Nozzle_Wash     <SEQ>
                drain           5
        END
WASH_2
        BEGIN
                Repeat          4
                                Add DCM 300
                                Drain 15
                End_Repeat
                Repeat 6
                                Add DMF 300
                                Drain 25
                End_Repeat
        END
REMOVE_FMOC
        BEGIN
                prime           piperidine
                Repeat          3
                set             0.08
                wait            15
                                Add piperidine 200
                                Wait 400
                                Drain 15
                End_Repeat
        END
WASH_3_DMF_PCN
        BEGIN
                Repeat          4
                                Add DMF 300
                                Drain 25
                End_Repeat
                Repeat          4
                                Add DCM 300
                                Drain 15
                End_Repeat
                Repeat          4
                                Add DMF 300
                                Drain 25
                End_Repeat
                Repeat          4
                                Add DCM 300
                                Drain 15
                End_Repeat
        END
NBS_ADDITION
        BEGIN
                prime           2-nitrobenzenesulfonyl chloride
                Repeat          3
                                set 0.08
                                wait 15
                                prime 2-nitrobenzenesulfonyl chloride
                                Add 2-nitrobenzenesulfonyl chloride 250
                                Wait 1200
                                Drain 15
                End_Repeat
                Nozzle_Wash     <SEQ>
                Nozzle_Wash     <SEQ>
        END
WASH_4_DMF_DCM
        BEGIN
                Repeat          6
                                Add DCM 250
                                Drain 15
                End_Repeat
                Repeat          4
                                Add DMF 300
                                Drain 25
                End_Repeat
                Repeat          4
                                Add DCM 300
                                Drain 15
                End_Repeat
                Repeat          4
                                Add DMF 300
                                Drain 25
                End_Repeat
                Repeat          4
                                Add DCM 300
                                Drain 15
                End_Repeat
        END
Linker_alkylation
        BEGIN
                next_sequence
                prime           <SEQ>
                prime           <ACT1>
                Repeat          4
                                set 0.08
                                wait 15
                                prime <SEQ>
                                prime <ACT1>
                                Add <SEQ> 125 + <ACT1> 125
                                Wait 1300
                                Drain 15
                End_Repeat
                Nozzle_Wash     <SEQ>
                Nozzle_Wash     <SEQ>
        END
WASH_5
        BEGIN
                Repeat          6
                                Add DCM 250
                                Drain 15
                End_Repeat
                Repeat          4
                                Add DMF 300
                                Drain 25
                End_Repeat
                Repeat          4
                                Add DCM 300
                                Drain 15
                End_Repeat
                Repeat          4
                                Add DMF 300
                                Drain 25
                End_Repeat
        END
REMOVE_NBS
        BEGIN
                Repeat          3
                                set 0.08
                                wait 15
                                prime mercaptoacetic acid
                                Add mercaptoacetic acid 250
                                Wait 1200
                                Drain 15
                End_Repeat
        END
WASH_6_DMF_DCM
```

-continued

```
        BEGIN
            Repeat      6
                        Add DMF 300
                        Drain 25
            End_Repeat
            Repeat      4
                        Add DCM 300
                        Drain 15
            End_Repeat
            Repeat      4
                        Add MEOH 300
                        Drain 15
            End_Repeat
            Repeat      4
                        Add DCM 300
                        Drain 15
            End_Repeat
            Repeat      6
                        Add DMF 300
                        Drain 25
            End_Repeat
        END
R3_FUNCTIONALIZATION
        BEGIN
            Next_Sequence
            Repeat      4
                        set 0.08
                        wait 15
                        prime <SEQ>
                        prime <ACT1>
                        Add <SEQ> 200 + <ACT1> 100
                        Wait 5400
                        Drain 15
            End_Repeat
        END
WASH_7_DMF_DCM_DMF
        BEGIN
            Repeat      4
                        Add DMF 300
                        Drain 25
            End_Repeat
            Repeat      4
                        Add DCM 300
                        Drain 15
            End_Repeat
            Repeat      4
                        Add MeOH 300
                        Drain 15
            End_Repeat
            Repeat      4
                        Add DCM 300
                        Drain 15
            End_Repeat
            Repeat      4
                        Add DMF 300
                        Drain 25
            End_Repeat
        END
REMOVE_TEOC
        BEGIN
            Repeat      3
                        set 0.08
                        wait 15
                        prime TBAF
                        Add TBAF 250
                        Wait 1200
                        Drain 40
            End_Repeat
        END
WASH_8_DMF_DCM_DMF
        BEGIN
            Repeat      4
                        Add DMF 200
                        Drain 40
            End_Repeat
            Repeat      4
                        Add MEOH 200
                        Drain 15
            End_Repeat
```

-continued

```
            Repeat      4
                        Add DCM 300
                        Drain 15
            End_Repeat
            Repeat      4
                        Add DMF 300
                        Drain 25
            End_Repeat
            Repeat      4
                        Add MEOH 300
                        Drain 15
            End_Repeat
            Repeat      4
                        Add DCM 300
                        Drain 15
            End_Repeat
            Repeat      6
                        Add DMF 300
                        Drain 25
            End_Repeat
        END
R4_FUNCTIONALIZATION
        BEGIN
            Next_Sequence
            Repeat      2
                        set 0.08
                        wait 15 {keep an eye on this}
                        prime <SEQ>
                        prime <ACT1>
                        Add <SEQ> 200
                        Wait 1800
                        Drain 15
            End_Repeat
        END
WASH_9_DMF_DCM
        BEGIN
            Repeat      4
                        Add DMF 300
                        Drain 25
            End_Repeat
            Repeat      4
                        Add DCM 300
                        Drain 15
            End_Repeat
            Repeat      4
                        Add MEOH 200
                        Drain 15
            End_Repeat
            Repeat      4
                        Add DMF 300
                        Drain 25
            End_Repeat
            Repeat      4
                        Add DCM 300
                        Drain 15
            End_Repeat
            Repeat      4
                        Add DMF 300
                        Drain 25
            End_Repeat
            Repeat      4
                        Add MEOH 300
                        Drain 15
            End_Repeat
            Repeat      4
                        Add DCM 300
                        Drain 15
            End_Repeat
        END
flush prime waste line
        begin
            prime       dcm
            drain       5
            prime       dmf
            drain       5
        end
END_W2
        BEGIN
                        Add DCM 300
```

```
                    -continued

Drain 60
                    Wait 10
        END
```

The additional controller sequence and reagent table files are constructed from any series of reagents, as specified in Brennan et al., such that the synthesizer automatically assembles the desired compounds using the above command file. This is accomplished by choosing a set of reagents to use, loading them into the appropriate bottles in the appropriate concentration, specifying this information into the reagent table file, and finally specifying the order of addition of reagents to each synthesis vessel in the sequence file. Appropriate reagents include: Any secondary amine functionalized resin (II), FMOC-amino acids to introduce the side chain functionality as $R_2$, any TEOC-protected ethanolamine (V) (including those derived from amino-acids to introduce the side chain as $R_3$, and sulfonyl halides, isocyanates, and activated guanylating agents such as bis (BOC)guanyl pyrazole for $R_4$ and $R_5$.

The appropriate reagents in appropriate solvent are then loaded onto the instrument, and the synthesis is started. After completion, the plate containing the resin bound compounds is removed, sealed, and trifluoroacetic acid containing 5% triisopropylsilane is added to each well, and the plated allowed to stand from 4–20 h. The filtrates are then collected into a 96-well plate, concentrated, and dried to afford the products.

Example 9

An example reagent table file

| Fmoc AA | | | | | | | |
|---|---|---|---|---|---|---|---|
| BEGIN | | | | | | | |
| 1 | N-FMOC-O-T-BUTYL-L-SERINE | N-FMOC-O-T-BUTYL-L-SERINE | 133 | 0.2 | 0.22 M HATU/ 0.5 M collidine/ DMF | 383.441 | |
| 2 | FMOC-L-LYS(BOC)-OH | FMOC-L-LYS(BOC)-OH | 133 | 0.2 | 0.22 M HATU/ 0.5 M collidine/ DMF | 468.55 | |
| 3 | FMOC-GLU(OTBU)-OH | FMOC-GLU(OTBU)-OH | 133 | 0.2 | 0.22 M HATU/ 0.5 M collidine/ DMF | 425.478 | |
| 4 | N-FMOC-O-T-BUTYL-L-TYROSINE | N-FMOC-O-T-BUTYL-L-TYROSINE | 133 | 0.2 | 0.22 M HATU/ 0.5 M collidine/ DMF | 459.539 | |
| END | | | | | | | |
| Linker | | | | | | | |
| BEGIN | | | | | | | |
| 12, 13 | TeocEA | TeocEA | 260 | 1 | | 205.3293 | |
| END | | | | | | | |
| RCO2H | | | | | | | |
| BEGIN | | | | | | | |
| 25 | thiophene-2-acetic acid | thiophene-2-acetic acid | 200 | 0.2 | .20 M HATU/0.6 M Collidine/ DMF | 142.177 | |
| 26 | BOC-imidazole-4-carboxylic acid | BOC-imidazole-4-carboxylic acid | 200 | 0.2 | .20 M HATU/0.6 M Collidine/ DMF | 212.2056 | |
| 27 | t-butoxyacetic acid | t-butoxyacetic acid | 200 | 0.2 | .20 M HATU/0.6 M Collidine/ DMF | 132.1598 | |
| 28 | nicotinic acid | nicotinic acid | 200 | 0.2 | .20 M HATU/0.6 M Collidine/ DMF | 123.11 | |
| 29 | BOC-beta-ALA-OH | BOC-beta-ALA-OH | 200 | 0.2 | .20 M HATU/0.6 M Collidine/ DMF | 189.21 | |
| 30 | 6-quinolinecarboxylic acid | 6-quinolinecarboxylic acid | 200 | 0.2 | .20 M HATU/0.6 M Collidine/ DMF | 173.17 | |
| END | | | | | | | |
| Supports | | | | | | | |
| BEGIN | | | | | | | |
| 0 | AG-Wang-piperazine | AG-Wang-piperazine | 1 | 1 | | 235.2632 | |
| 0 | AG-MB-benzylamine | AG-MB-benzylamine | 1 | 1 | | 242.2976 | |
| 0 | AG-MB-1-(2-aminoethyl)imidazolidin-2-one | AG-MB-1-(2-aminoethyl)imidazolidin-2-one | 1 | 1 | | 264.3044 | |
| 0 | AG-MB-2-pyridylmethylamine | AG-MB-2-pyridylmethylamine | 1 | 1 | | 243.2854 | |
| 0 | AG-MB-(2-aminoethyl)dimethylamine | AG-MB-(2-aminoethyl)dimethylamine | 1 | 1 | | 223.2951 | |
| 0 | AG-MB-N-acetylethylenediamine | AG-MB-N-acetylethylenediamine | 1 | 1 | | 237.2787 | |
| END | | | | | | | |
| Activators | | | | | | | |
| BEGIN | | | | | | | |
| 10, 11 | diethyl azodicarboxylate | diethyl azodicarboxylate | 275 | 1 | | 174.1565 | Activates Linker |

-continued

| | | | | | | | |
|---|---|---|---|---|---|---|---|
| END | | | | | | | |
| Deprotection | | | | | | | |
| BEGIN | | | | | | | |
| 18 | mercaptoacetic acid | mercaptoacetic acid | 180 | 0.5 | DMF + 1M DBU | | 92.11868 |
| 20 | piperidine | piperidine | 200 | 1 | DMF 8 | | 5.14937 |
| 22 | TBAF | TBAF | 100 | 0.2 | NMP | | 261.468 |
| END | | | | | | | |
| Protection | | | | | | | |
| BEGIN | | | | | | | |
| 14 | 2-nitrobenzenesulfonyl chloride | 2-nitrobenzenesulfonyl chloride | 300 | 0.2 | 0.2M DIEA/DMF | | 221.6212 |
| END | | | | | | | |
| Solvents {fixed} | | | | | | | |
| BEGIN | | | | | | | |
| 67 | DCM | DCM | 270 | 1 | | | 84.93294 |
| 66 | DMF | DMF | 220 | 1 | | | 73.09489 |
| 68 | MEOH | meoh | 270 | 1 | | | |
| END | | | | | | | |

Example 10

An example sequence file 1 23471 10 AG-MB-(2-aminoethyl)dimethylamine FMOC-GLU(OTBU)-OH TeocEA 6-quinolinecarboxylic acid BOC-beta-ALA-OH
2 23472 10 AG-MB-(2-aminoethyl)dimethylamine FMOC-GLU(OTBU)-OH TeocEA thiophene-2-acetic acid BOC-beta-ALA-OH
3 23473 10 AG-MB-(2-aminoethyl)dimethylamine FMOC-GLU(OTBU)-OH TeocEA BOC-beta-ALA-OH BOC-beta-ALA-OH
4 23474 10 AG-MB-(2-aminoethyl)dimethylamine FMOC-GLU(OTBU)-OH TeocEA t-butoxyacetic acid BOC-beta-ALA-OH
5 23475 10 AG-MB-(2-aminoethyl)dimethylamine EMOC-GLU(OTBU)-OH TeocEA 6-quinolinecarboxylic acid t-butoxyacetic acid
6 23476 10 AG-MB-(2-aminoethyl)dimethylamine FMOC-GLU(OTBU)-OH TeocEA thiophene-2-acetic acid t-butoxyacetic acid
7 23477 10 AG-MB-(2-aminoethyl)dimethylamine FMOC-GLU(OTBU)-OH TeocEA BOC-beta-ALA-OH t-butoxyacetic acid
8 23478 10 AG-MB-(2-aminoethyl)dimethylamine EMOC-GLU(OTBU)-OH TeocEA t-butoxyacetic acid t-butoxyacetic acid
9 23511 10 AG-MB-(2-aminoethyl)dimethylamine N-FMOC-O-T-BUTYL-L-SERINE TeocEA 6-quinolinecarboxylic acid nicotinic acid
10 23512 10 AG-MB-(2-aminoethyl)dimethylamine N-FMOC-O-T-BUTYL-L-SERINE TeocEA thiophene-2-acetic acid nicotinic acid
11 23513 10 AG-MB-(2-aminoethyl)dimethylamine N-FMOC-O-T-BUTYL-L-SERINE TeocEA BOC-beta-ALA-OH nicotinic acid
12 23514 10 AG-MB-(2-aminoethyl)dimethylamine N-FMOC-O-T-BUTYL-L-SERINE TeocEA t-butoxyacetic acid nicotinic acid
13 23515 10 AG-MB-(2-aminoethyl)dimethylamine N-FMOC-O-T-BUTYL-L-SERINE TeocEA 6-quinolinecarboxylic acid BOC-imidazole-4-carboxylic acid
14 23516 10 AG-MB-(2-aminoethyl)dimethylamine N-FMOC-O-T-BUTYL-L-SERINE TeocEA thiophene-2-acetic acid BOC-imidazole-4-carboxylic acid
15 23517 10 AG-MB-(2-aminoethyl)dimethylamine N-FMOC-O-T-BUTYL-L-SERINE TeocEA BOC-beta-ALA-OH BOC-imidazole-4-carboxylic acid
16 23518 10 AG-MB-(2-aminoethyl)dimethylamine N-FMOC-O-T-BUTYL-L-SERINE TeocEA t-butoxyacetic acid BOC-imidazole-4-carboxylic acid
17 23551 10 AG-MB-1-(2-aminoethyl)imidazolidin-2-one EMOC-L-LYS(BOC)-OH TeocEA 6-quinolinecarboxylic acid BOC-beta-ALA-OH
18 23552 10 AG-MB-1-(2-aminoethyl)imidazolidin-2-one FMOC-L-LYS(BOC)-OH TeocEA thiophene-2-acetic acid BOC-beta-ALA-OH
19 23553 10 AG-MB-1-(2-aminoethyl)imidazolidin-2-one FMOC-L-LYS(BOC)-OH TeocEA BOC-beta-ALA-OH BOC-beta-ALA-OH
20 23554 10 AG-MB-1-(2-aminoethyl)imidazolidin-2-one FMOC-L-LYS(BOC)-OH TeocEA t-butoxyacetic acid BOC -bet a-ALA-OH
21 23555 10 AG-MB-1-(2-aminoethyl)imidazolidin-2-one FMOC-L-LYS (BOC) -OH TeocEA 6-quinolinecarboxylic acid t-butoxyacetic acid
22 23556 10 AG-MB-1-(2-aminoethyl)imidazolidin-2-one FMOC-L-LYS(BOC)-OH TeocEA thiophene-2-acetic acid t-butoxyacetic acid
23 23557 10 AG-MB-1-(2-aminoethyl)imidazolidin-2-one EMOC-L-LYS(BOC)-OH TeocEA BOC-beta-ALA-OH t-butoxyacetic acid
24 23558 10 AG-MB-1-(2-aminoethyl)imidazolidin-2-one FMOC-L-LYS(BOC)-OH TeocEA t-butoxyacetic acid t-butoxyacetic acid
25 23591 10 AG-MB-1-(2-aminoethyl)imidazolidin-2-one N-FMOC-O-T-BUTYL-L-TYROSINE TeocEA 6-quinolinecarboxylic acid nicotinic acid
26 23592 10 AG-MB-1-(2-aminoethyl)imidazolidin-2-one N-FMOC-O-T-BUTYL-L-TYROSINE TeocEA thiophene-2-acetic acid nicotinic acid
27 23593 10 AG-MB-1-(2-aminoethyl)imidazolidin-2-one N-FMOC-O-T-BUTYL-L-TYROSINE TeocEA BOC-beta-ALA-OH nicotinic acid
28 23594 10 AG-MB-1-(2-aminoethyl)imidazolidin-2-one N-FMOC-O-T-BUTYL-L-TYROSINE TeocEA t-butoxyacetic acid nicotinic acid
29 23595 10 AG-MB-1-(2-aminoethyl)imidazolidin-2-one N-FMOC-O-T-BUTYL-L-TYROSINE TeocEA 6-quinolinecarboxylic acid BOC-imidazole-4-carboxylic acid
30 23596 10 AG-MB-1-(2-aminoethyl)imidazolidin-2-one N-FMOC-O-T-BUTYL-L-TYROSINE TeocEA thiophene-2-acetic acid BOC-imidazole-4-carboxylic acid
31 23597 10 AG-MB-1-(2-aminoethyl)imidazolidin-2-one N-FMOC-O-T-BUTYL-L-TYROSINE TeocEA BOC-beta-ALA-OH BOC-imidazole-4-carboxylic acid 32 23598 10 AG-MB-1-(2-aminoethyl)imidazolidin-2-one N-FMOC-O-T-BUTYL-L-TYROSINE TeocEA t-butoxyacetic acid BOC-imidazole-4-carboxylic acid
33 23615 10 AG-MB-2-pyridylmethylamine FMOC-L-LYS(BOC)-OH TeocEA 6-quinolinecarboxylic acid BOC-beta-ALA-OH
34 23616 10 AG-MB-2-pyridylmethylamine FMOC-L-LYS(BOC)-OH TeocEA thiophene-2-acetic acid BOC-beta-ALA-OH
35 23617 10 AG-MB-2-pyridylmethylamine FMOC-L-LYS(BOC)-OH TeocEA BOC-beta-ALA-OH BOC-beta-ALA-OH
36 23618 10 AG-MB-2-pyridylmethylamine FMOC-L-LYS(BOC)-OH TeocEA t-butoxyacetic acid BOC-beta-ALA-OH
37 23619 10 AG-MB-2-pyridylmethylamine FMOC-L-LYS(BOC)-OH TeocEA 6-quinolinecarboxylic acid t-butoxyacetic acid
38 23620 10 AG-MB-2-pyridylmethylamine FMOC-L-LYS(BOC)-OH TeocEA thiophene-2-acetic acid t-butoxyacetic acid
39 23621 10 AG-MB-2-pyridylmethylamine FMOC-L-LYS(BOC)-OH TeocEA BOC-beta-ALA-OH t-butoxyacetic acid
40 23622 10 AG-MB-2-pyridylmethylamine FMOC-L-LYS(BOC)-OH TeocEA t-butoxyacetic acid t-butoxyacetic acid
41 23631 10 AG-MB-2-pyridylmethylamine N-FMOC-O-T-BUTYL-L-SERINE TeocEA 6-quinolinecarboxylic acid BOC-beta-ALA-OH
42 23632 10 AG-MB-2-pyridylmethylamine N-FMOC-O-T-BUTYL-L-SERINE TeocEA thiophene-2-acetic acid BOC-beta-ALA-OH
43 23633 10 AG-MB-2-pyridylmethylamine N-FMOC-O-T-BUTYL-L-SERINE TeocEA BOC-beta-ALA-OH BOC-beta-ALA-OH
44 23634 10 AG-MB-2-pyridylmethylamine N-FMOC-O-T-BUTYL-L-SERINE TeocEA t-butoxyacetic acid BOC-beta-ALA-OH
45 23635 10 AG-MB-2-pyridylmethylamine N-FMOC-O-T-BUTYL-L-SERINE TeocEA 6-quinolinecarboxylic acid t-butoxyacetic acid
46 23636 10 AG-MB-2-pyridylmethylamine N-FMOC-O-T-BUTYL-L-SERINE TeocEA thiophene-2-acetic acid t-butoxyacetic acid
47 23637 10 AG-MB-2-pyridylmethylamine N-FMOC-O-T-BUTYL-L-SERINE TeocEA BOC-beta-ALA-OH t-butoxyacetic acid
48 23638 10 AG-MB-2-pyridylmethylamine N-FMOC-O-T-BUTYL-L-SERINE TeocEA t-butoxyacetic acid t-butoxyacetic acid
49 23671 10 AG-MB-benzylamine FMOC-GLU(OTBU)-OH TeocEA 6-quinolinecarboxylic acid nicotinic acid
50 23672 10 AG-MB-benzylamine FMOC-GLU(OTBU)-OH TeocEA thiophene-2-acetic acid nicotinic acid
51 23673 10 AG-MB-benzylamine FMOC-GLU(OTBU)-OH TeocEA BOC-beta-ALA-OH nicotinic acid
52 23674 10 AG-MB-benzylamine FMOC-GLU(OTBU)-OH TeocEA t-butoxyacetic acid nicotinic acid
53 23675 10 AG-MB-benzylamine FMOC-GLU(OTBU)-OH TeocEA 6-quinolinecarboxylic acid BOC-imidazole-4-carboxylic acid
54 23676 10 AG-MB-benzylamine FMOC-GLU(OTBU)-OH TeocEA thiophene-2-acetic acid BOC-imidazole-4-carboxylic acid
55 23677 10 AG-MB-benzylamine FMOC-GLU(OTBU)-OH TeocEA BOC-beta-ALA-OH BOC-imidazole-4-carboxylic acid
56 23678 10 AG-MB-benzylamine FMOC-GLU(OTBU)-OH TeocEA t-butoxyacetic acid BOC-imidazole-4-carboxylic acid
57 23711 10 AG-MB-benzylamine N-FMOC-O-T-BUTYL-L-TYROSINE TeocEA 6-quinolinecarboxylic acid BOC-beta-ALA-OH
58 23712 10 AG-MB-benzylamine N-FMOC-O-T-BUTYL-L-TYROSINE TeocEA thiophene-2-acetic acid BOC-beta-ALA-OH
59 23713 10 AG-MB-benzylamine N-FMOC-O-T-BUTYL-L-TYROSINE TeocEA BOC-beta-ALA-OH BOC-beta-ALA-OH
60 23714 10 AG-MB-benzylamine N-FMOC-O-T-BUTYL-L-TYROSINE TeocEA t-butoxyacetic acid BOC-beta-ALA-OH
61 23715 10 AG-MB-benzylamine N-FMOC-O-T-BUTYL-L-TYROSINE TeocEA 6-quinolinecarboxylic acid t-butoxyacetic acid
62 23716 10 AG-MB-benzylamine N-FMOC-O-T-BUTYL-L-TYROSINE TeocEA thiophene-2-acetic acid t-butoxyacetic acid
63 23717 10 AG-MB-benzylamine N-FMOC-O-T-BUTYL-L-TYROSINE TeocEA BOC-beta-ALA-OH t-butoxyacetic acid
64 23718 10 AG-MB-benzylamine N-FMOC-O-T-BUTYL-L-TYROSINE TeocEA t-butoxyacetic acid t-butoxyacetic acid
65 23751 10 AG-MB-N-acetylethylenediamine FMOC-L-LYS(BOC)-OH TeocEA 6-quinolinecarboxylic acid nicotinic acid
66 23752 10 AG-MB-N-acetylethylenediamine FMOC-L-LYS(BOC)-OH TeocEA thiophene-2-acetic acid nicotinic acid
67 23753 10 AG-MB-N-acetylethylenediamine FMOC-L-LYS(BOC)-OH TeocEA BOC-beta-ALA-OH nicotinic acid
68 23754 10 AG-MB-N-acetylethylenediamine FMOC-L-LYS(BOC)-OH TeocEA t-butoxyacetic acid nicotinic acid
69 23755 10 AG-MB-N-acetylethylenediamine FMOC-L-LYS(BOC)-OH TeocEA 6-quinolinecarboxylic acid BOC-imidazole-4-carboxylic acid
70 23756 10 AG-MB-N-acetylethylenediamine FMOC-L-LYS(BOC)-OH TeocEA thiophene-2-acetic acid BOC-imidazole-4-carboxylic acid
71 23757 10 AG-MB-N-acetylethylenediamine FMOC-L-LYS(BOC)-OH TeocEA BOC-beta-ALA-OH BOC-imidazole-4-carboxylic acid
72 23758 10 AG-MB-N-acetylethylenediamine FMOC-L-LYS(BOC)-OH TeocEA t-butoxyacetic acid BOC-imidazole-4-carboxylic acid
73 23783 10 AG-MB-N-acetylethylenediamine N-FMOC-O-T-BUTYL-L-TYROSINE TeocEA 6-quinolinecarboxylic acid nicotinic acid
74 23784 10 AG-MB-N-acetylethylenediamine N-FMOC-O-T-BUTYL-L-TYROSINE TeocEA thiophene-2-acetic acid nicotinic acid
75 23785 10 AG-MB-N-acetylethylenediamine N-FMOC-O-T-BUTYL-L-TYROSINE TeocEA BOC-beta-ALA-OH nicotinic acid
76 23786 10 AG-MB-N-acetylethylenediamine N-FMOC-O-T-BUTYL-L-TYROSINE TeocEA t-butoxyacetic acid nicotinic acid
77 23787 10 AG-MB-N-acetylethylenediamine N-FMOC-O-T-BUTYL-L-TYROSINE TeocEA 6-quinolinecarboxylic acid BOC-imidazole-4-carboxylic acid 78 23788 10 AG-MB-N-acetylethylenediamine N-FMOC-O-T-BUTYL-L-TYROSINE TeocEA thiophene-2-acetic acid BOC-imidazole-4-carboxylic acid
79 23789 10 AG-MB-N-acetylethylenediamine N-FMOC-O-T-BUTYL-L-TYROSINE TeocEA BOC-beta-ALA-OH BOC-imidazole-4-carboxylic acid
80 23790 10 AG-MB-N-acetylethylenediamine N-FMOC-O-T-BUTYL-L-TYROSINE TeocEA t-butoxyacetic acid BOC-imidazole-4-carboxylic acid
81 23791 10 AG-Wang-piperazine FMOC-GLU(OTBU)-OH TeocEA 6-quinolinecarboxylic acid BOC-beta-ALA-OH
82 23792 10 AG-Wang-piperazine FMOC-GLU(OTBU)-OH TeocEA thiophene-2-acetic acid BOC-beta-ALA-OH
83 23793 10 AG-Wang-piperazine FMOC-GLU(OTBU)-OH TeocEA BOC-beta-ALA-OH BOC-beta-ALA-OH
84 23794 10 AG-Wang-piperazine FMOC-GLU(OTBU)-OH TeocEA t-butoxyacetic acid BOC-beta-ALA-OH
85 23795 10 AG-Wang-piperazine FMOC-GLU(OTBU)-OH TeocEA 6-quinolinecarboxylic acid t-butoxyacetic acid
86 23796 10 AG-Wang-piperazine FMOC-GLU(OTBU)-OH TeocEA thiophene-2-acetic acid t-butoxyacetic acid
87 23797 10 AG-Wang-piperazine FMOC-GLU(OTBU)-OH TeocEA BOC-beta-ALA-OH t-butoxyacetic acid
88 23798 10 AG-Wang-piperazine FMOC-GLU(OTBU)-OH TeocEA t-butoxyacetic acid t-butoxyacetic acid
89 23831 10 AG-Wang-piperazine N-FMOC-O-T-BUTYL-L-SERINE TeocEA 6-quinolinecarboxylic acid nicotinic acid
90 23832 10 AG-Wang-piperazine N-FMOC-O-T-BUTYL-L-SERINE TeocEA thiophene-2-acetic acid nicotinic acid
91 23833 10 AG-Wang-piperazine N-FMOC-O-T-BUTYL-L-SERINE TeocEA BOC-beta-ALA-OH nicotinic acid
92 23834 10 AG-Wang-piperazine N-FMOC-O-T-BUTYL-L-SERINE TeocEA t-butoxyacetic acid nicotinic acid
93 23835 10 AG-Wang-piperazine N-FMOC-O-T-BUTYL-L-SERINE TeocEA 6-quinolinecarboxylic acid BOC-imidazole-4-carboxylic acid
94 23836 10 AG-Wang-piperazine N-FMOC-O-T-BUTYL-L-SERINE TeocEA thiophene-2-acetic acid BOC-imidazole-4-carboxylic acid
95 23837 10 AG-Wang-piperazine N-FMOC-O-T-BUTYL-L-SERINE TeocEA BOC-beta-ALA-OH BOC-imidazole-4-carboxylic acid
96 23838 10 AG-Wang-piperazine N-FMOC-O-T-BUTYL-L-SERINE TeocEA t-butoxyacetic acid BOC-imidazole-4-carboxylic acid Example 11

Functionality generated and reagents used in example plate synthesis

| R # | Entry No. | Functionality generated | Reagent | CAS Reg. | Mol. Formula |
|---|---|---|---|---|---|
| 1 | 11 | piperazine | AG-Wang-piperazine (IIg) | | |
| 1 | 12 | benzyl | AG-MB-benzylamine (IIa) | | |
| 1 | 13 | 1-(2-ethyl)-imidazolidin-2-one | AG-MB-1-(2-aminoethyl)-imidazolidin-2-one (IIe) | | |
| 1 | 14 | 2-pyridylmethyl | AG-MB-2-pyridyl-methylamine (IIf) | | |
| 1 | 15 | 1-(2-Dimethyl-amino) ethyl | AG-MB-(2-aminoethyl)-dimethylamine (IIc) | | |
| 1 | 16 | 2-(N-acetylamino)ethyl | AG-MB-N-acetyl-ethylene-diamine (IId) | | |
| 2 | 1 | (S)-hydroxymethyl | N-FMOC-O-t-butyl-L-Serine | 71989-33-8 | C22H25NO5 |
| 2 | 2 | (S)-4-aminobutyl | N-FMOC-L-Lys(BOC)-OH | 92122-45-7 | C26H32N2O6 |
| 2 | 3 | (S)-2-carboxyethyl | N-FMOC-Glu(O-t-butyl)-OH | 71989-18-9 | C24H27NO6 |
| 2 | 4 | (S)-hydroxybenzyl | N-FMOC-O-t-butyl-L-Tyr | 71989-38-3 | C28H29NO5 |
| 3 | 17 | H | N-TEOC-ethanolamine (Va) | | C8H19NO3Si |
| 4 | 5 | thiophene-2-acetyl | thiophene-2-acetic acid | 1918-77-0 | C6H6O2S |
| 4 | 7 | hydroxyacetyl | t-butoxy-acetic acid | 13211-32-0 | C6H12O3 |
| 4 | 9 | 3-aminopropionyl | BOC-β-Ala-OH | 3303-84-2 | C8H15NO4 |
| 4 | 10 | 6-quinolinecarboxyl | 6-quinoline carboxylic acid | 10349-57-3 | C10H7NO2 |
| 5 | 6 | imidazole-4-carboxyl | BOC-imidazole-4-carboxylic acid | | C9H12N2O4 |
| 5 | 7 | hydroxyacetyl | t-butoxy-acetic acid | 13211-32-0 | C6H12O3 |
| 5 | 8 | nicotinoyl | nicotinic acid | 59-67-6 | C6H5NO2 |
| 5 | 9 | 3-aminopropionyl | BOC-β-Ala-OH | 3303-84-2 | C8H15NO4 |

CAS Reg. = Cas Registry Number

Example 12

Yield and MS data on selected compounds from example plate synthesis

| W1 | W2 | Y | MS | $R_1$ | $R_2$ | $R_3$ | $R_4$ | $R_5$ |
|---|---|---|---|---|---|---|---|---|
| A01 | 1.7 | 486 | 15 | 3 | 17 | 10 | 9 | |
| A02 | 8.5 | 180 | 455 (M + H, 100) | 15 | 3 | 17 | 5 | 9 |
| A03 | 3.4 | 81 | 402 (M + H, 100) | 15 | 3 | 17 | 9 | 9 |
| A04 | 6.5 | 160 | 389 (M + H, 100) | 15 | 3 | 17 | 7 | 9 |
| A05 | 2.5 | 51 | 473 | 15 | 3 | 17 | 10 | 7 |
| A06 | 7.8 | 170 | 442 (M + H, 100) | 15 | 3 | 17 | 5 | 7 |
| A07 | 3.4 | 84 | 389 (M + H, 100) | 15 | 3 | 17 | 9 | 7 |
| A08 | 5.2 | 132 | 376 (M + H, 100) | 15 | 3 | 17 | 7 | 7 |
| A09 | 1.5 | 30 | 478 (M + H, 100) | 15 | 1 | 17 | 10 | 8 |
| A10 | 7.5 | 162 | 447 (M + H, 100) | 15 | 1 | 17 | 5 | 8 |

-continued

| W1 | W2 | Y | MS | R₁ | R₂ | R₃ | R₄ | R₅ |
|---|---|---|---|---|---|---|---|---|
| A11 | 2.0 | 49 |  | 15 | 1 | 17 | 9 | 8 |
| A12 | 6.1 | 153 |  | 15 | 1 | 17 | 7 | 8 |
| B01 | 2.6 | 54 | 467 (M + H, 100) | 15 | 1 | 17 | 10 | 6 |
| B02 | 7.7 | 170 | 436 (M + H, 100) | 15 | 1 | 17 | 5 | 6 |
| B03 | 3.7 | 93 |  | 15 | 1 | 17 | 9 | 6 |
| B04 | 5.5 | 142 | 370 (M + H, 100) | 15 | 1 | 17 | 7 | 6 |
| B05 | 2.2 | 42 | 526 | 13 | 2 | 17 | 10 | 9 |
| B06 | 10 | 202 | 495 (M + H, 100) | 13 | 2 | 17 | 5 | 9 |
| B07 | 5.6 | 127 | 442 (M + H, 100) | 13 | 2 | 17 | 9 | 9 |
| B08 | 6.6 | 154 | 429 (M + H, 100) | 13 | 2 | 17 | 7 | 9 |
| B09 | 3.1 | 60 | 513 | 13 | 2 | 17 | 10 | 7 |
| B10 | 9.4 | 195 | 482 (M + H, 100) | 13 | 2 | 17 | 5 | 7 |
| B11 | 4.7 | 109 | 429 (M + H, 100) | 13 | 2 | 17 | 9 | 7 |
| B12 | 3.4 | 82 | 416 (M + H, 100) | 13 | 2 | 17 | 7 | 7 |
| C01 | 2.0 | 34 | 595 | 13 | 4 | 17 | 10 | 8 |
| C02 | 11.3 | 200 | 564 (M + H, 100) | 13 | 4 | 17 | 5 | 8 |
| C03 | 5.7 | 111 | 511 (M + H, 100) | 13 | 4 | 17 | 9 | 8 |
| C04 | 7.1 | 142 | 498 (M + H, 100) | 13 | 4 | 17 | 7 | 8 |
| C05 | 1.6 | 27 | 584 | 13 | 4 | 17 | 10 | 6 |
| C06 | 14.6 | 264 | 553 (M + H, 100) | 13 | 4 | 17 | 5 | 6 |
| C07 | 8.5 | 170 | 500 (M + H, 82) | 13 | 4 | 17 | 9 | 6 |
| C08 | 8.2 | 168 | 487 (MtH, 59) | 13 | 4 | 17 | 7 | 6 |
| C09 | 0.8 | 16 |  | 14 | 2 | 17 | 10 | 9 |
| C10 | 2.8 | 59 | 474 (M + H, 100) | 14 | 2 | 17 | 5 | 9 |
| C11 | 1.2 | 28 |  | 14 | 2 | 17 | 9 | 9 |
| C12 | 1.8 | 44 | 408 (M + H, 100) | 14 | 2 | 17 | 7 | 9 |
| D01 | 1.5 | 30 | 492 | 14 | 2 | 17 | 10 | 7 |
| D02 | 2.5 | 54 | 461 (M + H, 100) | 14 | 2 | 17 | 5 | 7 |
| D03 | 0.5 | 12 |  | 14 | 2 | 17 | 9 | 7 |
| D04 | 1.9 | 48 | 395 (M + H, 100) | 14 | 2 | 17 | 7 | 7 |
| D05 | 0.9 | 19 |  | 14 | 1 | 17 | 10 | 9 |
| D06 | 1.7 | 39 | 433 (M + H, 100) | 14 | 1 | 17 | 5 | 9 |
| D07 | 0.7 | 18 |  | 14 | 1 | 17 | 9 | 9 |
| D08 | 1.6 | 44 | 367 (M + H, 100) | 14 | 1 | 17 | 7 | 9 |
| D09 | 1.9 | 42 | 451 | 14 | 1 | 17 | 10 | 7 |
| D10 | 2.4 | 57 | 420 (M + H, 100) | 14 | 1 | 17 | 5 | 7 |
| D11 | 1.2 | 33 | 367 | 14 | 1 | 17 | 9 | 7 |
| D12 | 1.9 | 54 | 354 (M + H, 100) | 14 | 1 | 17 | 7 | 7 |
| E01 | 2.4 | 44 | 539 | 12 | 3 | 17 | 10 | 8 |
| E02 | 6.4 | 126 | 508 (M + H, 99) | 12 | 3 | 17 | 5 | 8 |
| E03 | 3.3 | 72 | 455 (M + H, 100) | 12 | 3 | 17 | 9 | 8 |
| E04 | 4.4 | 99 | 442 (M + H, 100) | 12 | 3 | 17 | 7 | 8 |
| E05 | 2.6 | 49 | 528 | 12 | 3 | 17 | 10 | 6 |
| E06 | 6.6 | 133 | 497 (M + H, 45) | 12 | 3 | 17 | 5 | 6 |
| E07 | 4.3 | 97 | 444 (M + H, 100) | 12 | 3 | 17 | 9 | 6 |
| E08 | 1.1 | 25 | 431 (M + H, 72) | 12 | 3 | 17 | 7 | 6 |
| E09 | 1.9 | 35 | 539 | 12 | 4 | 17 | 10 | 9 |
| E10 | 8.7 | 171 | 508 (M + H, 100) | 12 | 4 | 17 | 5 | 9 |
| E11 | 4.9 | 108 | 455 (M + H, 100) | 12 | 4 | 17 | 9 | 9 |
| E12 | 7.5 | 169 | 442 (M + H, 100) | 12 | 4 | 17 | 7 | 9 |
| F01 | 2.4 | 46 | 526 | 12 | 4 | 17 | 10 | 7 |
| F02 | 13.2 | 266 | 495 | 12 | 4 | 17 | 5 | 7 |
| F03 | 6.6 | 149 | 442 (M + H, 100) | 12 | 4 | 17 | 9 | 7 |
| F04 | 9.5 | 221 | 429 (M + H, 64) | 12 | 4 | 17 | 7 | 7 |
| F05 | 1.4 | 26 | 533 | 16 | 2 | 17 | 10 | 8 |
| F06 | 7.7 | 153 | 502 (M + H, 100) | 16 | 2 | 17 | 5 | 8 |
| F07 | 4.1 | 91 | 449 (M + H, 100) | 16 | 2 | 17 | 9 | 8 |
| F08 | 4.9 | 112 | 436 (M + H, 100) | 16 | 2 | 17 | 7 | 8 |
| F09 | 2.3 | 44 | 522 | 16 | 2 | 17 | 10 | 6 |
| F10 | 6.7 | 136 | 491 (M + H, 100) | 16 | 2 | 17 | 5 | 6 |
| F11 | 7.5 | 171 | 438 (M + H, 100) | 16 | 2 | 17 | 9 | 6 |
| F12 | 5.8 | 136 | 425 (M + H, 100) | 16 | 2 | 17 | 7 | 6 |
| G01 | 2.0 | 35 | 568 | 16 | 4 | 17 | 10 | 8 |
| G02 | 8.3 | 154 | 537 (M + H, 100) | 16 | 4 | 17 | 5 | 8 |
| G03 | 4.1 | 85 | 484 (M + H, 100) | 16 | 4 | 17 | 9 | 8 |
| G04 | 5.5 | 117 | 471 (M + H, 100) | 16 | 4 | 17 | 7 | 8 |
| G05 | 1.9 | 34 | 557 | 16 | 4 | 17 | 10 | 6 |
| G06 | 10.1 | 192 | 526 (M + H, 100) | 16 | 4 | 17 | 5 | 6 |
| G07 | 4.6 | 97 | 473 (M + H, 100) | 16 | 4 | 17 | 9 | 6 |
| G08 | 6.9 | 150 | 460 (M + H, 81) | 16 | 4 | 17 | 7 | 6 |
| G09 | 9.3 | 192 | 484 | 11 | 3 | 17 | 10 | 9 |
| G10 | 5.6 | 123 | 453 | 11 | 3 | 17 | 5 | 9 |
| G11 | 10.3 | 257 | 400 (M + H, 47) | 11 | 3 | 17 | 9 | 9 |
| G12 | 6.9 | 178 | 387 (M + H, 72) | 11 | 3 | 17 | 7 | 9 |
| H01 | 5.5 | 117 | 471 | 11 | 3 | 17 | 10 | 7 |
| H02 | 3.5 | 79 |  | 11 | 3 | 17 | 5 | 7 |
| H03 | 12.0 | 310 | 387 (M + H, 46) | 11 | 3 | 17 | 9 | 7 |
| H04 | 6.4 | 171 | 374 (M + H, 84) | 11 | 3 | 17 | 7 | 7 |
| H05 | 7.8 | 164 | 476 | 11 | 1 | 17 | 10 | 8 |
| H06 | 6.1 | 137 | 445 | 11 | 1 | 17 | 5 | 8 |
| H07 | 7.0 | 178 | 392 | 11 | 1 | 17 | 9 | 8 |
| H08 | 8.3 | 219 | 379 (M + H, 100) | 11 | 1 | 17 | 7 | 8 |
| H09 | 10.9 | 234 | 465 | 11 | 1 | 17 | 10 | 6 |
| H10 | 7.2 | 166 | 434 | 11 | 1 | 17 | 5 | 6 |
| H11 | 8.8 | 231 | 381 | 11 | 1 | 17 | 9 | 6 |
| H12 | 8.5 | 231 | 368 (M + H, 100) | 11 | 1 | 17 | 7 | 6 |

W1 = Well; W2 = Weight (mg); Y = Yield (%);

MS=Expected (Found, relative intensity)

Compound in well E10 exhibited 99% in an MIC *S. pyogenes* assay.

Example 13

Table of reagents used to construct a library of compounds

| P | Reagent | CAS Reg. | MF |
|---|---|---|---|
| SEQ1 | (IIa) |  |  |
| SEQ1 | (IIb) |  |  |
| SEQ1 | (IIc) |  |  |
| SEQ1 | (IId) |  |  |
| SEQ1 | (IIe) |  |  |
| SEQ1 | (IIf) |  |  |
| SEQ1 | (IIg) |  |  |
| SEQ2 | N-FMOC-D-Ser(t-butyl)-OH | 128107-47-1 | C22H25NO5 |
| SEQ2 | N-FMOC-O-t-butyl-L-Ser | 71989-33-8 | C22H25NO5 |
| SEQ2 | N-FMOC-D-Tyr(t-butyl)-OH | 118488-18-9 | C28H29NO5 |
| SEQ2 | N-FMOC-O-t-butyl-L-Tyr | 71989-38-3 | C28H29NO5 |
| SEQ2 | N-FMOC-D-Arg(PMC)-OH | 119831-72-0 | C35H42N4O7S |
| SEQ2 | N-FMOC-Arg(PMC)-OH | 119831-72-0 | C35H42N4O7S |
| SEQ2 | N-FMOC-D-Leu-OH | 114360-54-2 | C21H23NO4 |
| SEQ2 | N-FMOC-L-Leu | 35661-60-0 | C21H23NO4 |
| SEQ2 | N-FMOC-D-Trp(BOC)-OH | 143824-78-6 | C31H30N2O6 |
| SEQ2 | N-FMOC-Trp(BOC)-OH | 143824-78-6 | C31H30N2O6 |
| SEQ2 | N-FMOC-D-His(BOC)-OH | 71989-26-9 | C26H27N3O6 |
| SEQ2 | N-FMOC-His(BOC)-OH | 71989-26-9 | C26H27N3O6 |
| SEQ2 | N-FMOC-D-Asp(O-t-butyl)-OH | 112883-39-3 | C23H25NO6 |
| SEQ2 | N-FMOC-L-Aspartic acid-β-t-butyl ester | 71989-14-5 | C23H25NO6 |
| SEQ2 | N-FMOC-D-Asn(TRT)-OH | 132388-59-1 | C38H32N2O5 |
| SEQ2 | N-FMOC-Asn(TRT)-OH | 132388-59-1 | C38H32N2O5 |
| SEQ2 | N-α-FMOC-N-β-(BOC)-D-diaminopropionic acid |  | C23H26N2O6 |
| SEQ2 | N-α-FMOC-N-β-(BOC)-L-diaminopropionic acid |  | C23H26N2O6 |
| SEQ2 | N-FMOC-p-amino-D-Phe(BOC)-OH |  | C29H30N2O6 |
| SEQ2 | N-FMOC-p-amino-Phe(BOC)-OH |  | C29H30N2O6 |
| SEQ3 | N-TEOC-ethanolamine |  | C8H19NO3Si |
| SEQ4 | BOC-isonipecotic acid | 84358-13-4 | C11H19NO4 |
| SEQ4 | Isobutyraldehyde | 78-84-2 | C4H8O |
| SEQ4 | 3-pyridinecarboxaldehyde | 500-22-1 | C6H5NO |

-continued

Table of reagents used to construct a library of compounds

| P | Reagent | CAS Reg. | MF |
|---|---------|----------|-----|
| SEQ4 | 3,5-bis(trifluoromethyl)-benzaldehyde | 401-95-6 | C9H4F6O |
| SEQ4 | Hydantoic acid | 462-60-2 | C3H6N2O3 |
| SEQ4 | BOC-Ser(t-butyl)-OH | 13734-38-8 | C12H23NO5 |
| SEQ4 | t-Butoxyacetic acid | 13211-32-0 | C6H12O3 |
| SEQ4 | Nalidixic acid | 389-08-2 | C12H12N2O3 |
| SEQ4 | 3-pyridylacetic acid hydrochloride | 6419-36-9 | C7H7NO2.Cl |
| SEQ4 | Thymine-1-acetic acid | 20924-05-4 | C7H8N2O4 |
| SEQ5 | (R)-(−)-2,2-dimethyl-5-oxo-1,3-dioxolane-4-acetic acid | 113278-68-5 | C7H10O5 |
| SEQ5 | (S)-(+)-2,2-dimethyl-5-oxo-1,3-dioxolane-4-acetic acid | 113278-68-5 | C7H10O5 |
| SEQ5 | N-BOC-L-Homoserine | 41088-86-2 | C9H17NO5 |
| SEQ5 | BOC-isonipecotic acid | 84358-13-4 | C11H19NO4 |
| SEQ5 | bis(BOC-3,5-diaminobenzoic acid) | 111331-82-9 | C17H24N2O6 |
| SEQ5 | BOC-Thr(t-butyl)-OH | 13734-40-2 | C13H25NO5 |
| SEQ5 | 4-methoxybenzyl isocyanate | 56651-60-6 | C9H9NO2 |
| SEQ5 | BOC-imidazole-4-carboxylic acid | | C9H12N2O4 |
| SEQ5 | bis-BOC-guanyl pyrazole | | C14H22N4O4 |
| SEQ5 | 1-fluorenecarboxylic acid | 6276-03-5 | C14H10O2 |
| SEQ5 | Orotic acid | 65-86-1 | C5H4N2O4 |
| SEQ5 | Nicotinic acid | 59-67-6 | C6H5NO2 |
| SEQ5 | Nalidixic acid | 389-08-2 | C12H12N2O3 |
| SEQ5 | 6-Quinolinecarboxylic acid | 10349-57-2 | C10H7NO2 |
| SEQ5 | Thymine-1-acetic acid | 20924-05-4 | C7H8N2O4 |
| SEQ5 | (None, leaves H in the product) | | |
| SEQ5 | 3-({[4-methoxyphenyl)-methyl]amino}carbonyl-amino)benzoic acid | | C16H16N2O4 |

P = position; CAS Reg. = CAS Registry Number; MF = Molecular Formula

BIOLOGICAL ASSAYS

Assay 1: *Staphylococcus aureus* antimicrobial assay

*Staphylococcus aureus* is known to cause localized skin infections as a result of poor hygiene, minor trauma, psoriasis or eczema. It also causes respiratory infections, pneumonia, toxic shock syndrome and septicemia. It is a common cause of acute food poisoning. It exhibits rapid emergence of drug resistance to penicillin, cephalosporin, vancomycin and nafcillin.

In this assay, the strain *S. aureus* ATCC 25923 (American Type Culture Collection) is used. To initiate the exponential phase of bacterial growth prior to the assay, a sample of bacteria grown overnight at 37° C. in typtocase soy broth (BBL). This bacteria is then used to reinoculate sample wells of 96-well microtiter plates. The assays are carried out in the 96-well microtiter plates in 150 μL volume with approximately $1 \times 10^6$ cells per well.

Bacteria in typtocase soy broth (75 μL) is added to the compound mixtures in solution in 75 μL water/4% DMSO in the individual well of the microtiter plate. Final concentrations of the compound mixtures are 25 μM, 10 μM and 1 μM. Each concentration of the compound mixtures are assayed in triplicate. The plates are incubated at 37 C and growth monitored over a 24 hour period by measuring the optical density at 595 nm using a BioRad model 3550 UV microplate reader. The percentage of growth relative to a well containing no compound is determined. Ampicillin and tetracycline antibiotic positive controls are concurrently tested in each screening assay.

Assay 2: *Streptococcus Pyogenes* antimicrobial assay

In this assay, the strain *S. pyogenes* ATCC 14289 (American Type Culture Collection) is used. To initiate the exponential phase of bacterial growth prior to the assay, a sample of bacteria is grown overnight at 37° C. in 1× Todd-Hewitt broth. This bacteria is then used to reinoculate sample wells of 96-well microtiter plates. The assays are carried out in the 96-well microtiter plates in 150 μL volume with approximately $1 \times 10^6$ cells per well.

Bacteria in 1× Todd-Hewitt broth (75 μL) is added to the compound mixtures in solution in 75 μL water in the individual well of the microtiter plate. Final concentrations of the compound mixtures are 25 μM, 10 μM and 1 μM. Each concentration of the compound mixtures are assayed in triplicate. The plates are incubated at 37° C. and growth monitored over a 24 hour period by measuring the optical density at 595 nm using a BioRad model 3550 UV microplate reader. The percentage of growth relative to a well containing no compound is determined. Ampicillin and tetracycline antibiotic positive controls are concurrently tested in each screening assay.

Assay 3: *E. coli* imp- antimicrobial assay

In this assay, the strain *E. coli* imp- obtained from Spenser Bensen (Sampson, B. A., Misra, R. & Benson, S. A. (1989), Genetics, 122, 491–501, Identification and characterization of a new gene of *Escherichia coil* K-12 involved in outer membrane permeability) is used. To initiate the exponential phase of bacterial growth prior to the assay, a sample of bacteria was grown overnight at 37° C. in Luria broth and then used to reinoculate sample wells of 96-well microtiter plates. The assays were carried out in the 96-well microtiter plates in 150 μL volume with approximately $1 \times 10^6$ cells per well.

Bacteria in Luria broth (75 μL) was added to the compound mixtures in solution in 75 μL water in the individual well of the microtiter plate. Final concentrations of the compound mixtures were 25 μM, 10 μM and 1 μM. Each concentration of the compound mixtures were assayed in triplicate. The plates were incubated at 37° C. and growth monitored over a 24 hour period by measuring the optical density at 595 nm using a BioRad model 3550 UV microplate reader. The percentage of growth relative to a well containing no compound was determined. Ampicillin and tetracycline antibiotic positive controls were concurrently tested in each screening assay.

Assay 4: *C. albicans* antifungal assay

In this assay, the strain *C. albicans* ATCC 10231 (American Type Culture Collection) is used. To initiate the exponential phase of yeast growth prior to the assay, a sample of yeast is grown overnight at 37° C. in YM media. This yeast is then used to reinoculate sample wells of 96-well microtiter plates. The assays are carried out in the 96-well microtiter plates in 150 μL volume with approximately $1 \times 10^6$ cells per well.

Yeast in YM media (75 μL) is added to the compound mixtures in solution in 75 μL water in the individual well of the microtiter plate. Final concentrations of the compound mixtures are 25 μM, 10 μM and 1 μM. Each concentration of the compound mixtures are assayed in triplicate. The plates are incubated at 37° C. and growth monitored over a 24 hour period by measuring the optical density at 595 nm using a BioRad model 3550 UV microplate reader. The percentage of growth relative to a well containing no compound is determined. Amphotericin B positive control is concurrently tested in each screening assay.

Assay 5: tat/TAR inhibition assay

The effects of combinatorial libraries, and individual members thereof, on HIV tat/TAR, RNA/protein interactions are examined using a rapid and reproducible binding assay. The assay consists of a biotinylated truncated version of the HIV-1 TAR stem-loop, which is anchored to the wells of a 96 well ELISA plate which has been coated with streptavidin. The TAR RNA is recognized by the HIV-1 protein tat and the amount of tat bound is quantitated using an antibody raised against tat and a secondary antibody conjugated to an alkaline phosphatase or HRP enzyme to produce a calorimetric reaction.

Materials:

A 39 residue tat peptide (aa 49–85 of HIV tat protein). This is the C terminal basic binding domain of the tat protein. This peptide was synthesized by a contract lab.

A 30 base RNA oligonucleotide consisting of the bulge and stem/loop structure of HIV TAR which has also been Biotin conjugated. This RNA oligonucleotide was synthesized in house.

A biotinylated HIV RRE RNA oligonucleotide synthesized in house.

Binding buffer: 40 mM Tris-HCl (pH 8.0), 0.01% NP-40, 20% glycerol, 1.5 mM MgCl, 0.01% NaN3, 50 mM KCl.

Streptavidin coated 96 well microtitre plates (Elkay Labsystems).

Protein A/G alkaline phosphatase (Pierce).

Anti tat antiserum (BioDesign).

PNPP substrate (Pierce).

Methods:

To each well of a Streptavidin coated 96 well ELISA plate is added 200 μl of a solution of the 30 base TAR sequence (20 nM) in binding buffer. The plate is incubated at 4° C. for 1 hour. The biotintylated HIV RRE RNA oligonucleotide is bound to selected wells as a negative control RNA. The plate is washed with binding buffer three times and 100 μl of a 100 nM solution of the 39 residue tat peptide in binding buffer is added to each well.

Combinatorial libraries as mixtures, or discrete members thereof, are added to selected wells of the plate at initial concentrations of 100 μM. The plate is incubated for 1 hour at room temperature.

The plate is washed with binding buffer three times and blocked with binding buffer +5% FCS. 100 μl of tat antiserum diluted 1:700 in binding buffer is added to the wells of the plate and the plate is incubated for 1.5 hours at 4° C. The plate is washed three times with binding buffer and 150 μL of a solution of protein A/G alkaline phosphatase diluted 1:5000 in binding buffer is added to each well. The plate is incubated for 1.5 hours at 4° C. followed by washing three times with binding buffer. 150 μL of PNPP substrate is added to each well and the plate is incubated for 1 hour at 37° C. The absorbance of each well is read in a multiwell plate reader.

Assay 6: Bacterial DNA Gyrase antimicrobial mechanistic assay

DNA gyrase is a bacterial enzyme which can introduce negative supercoils into DNA utilizing the energy derived from ATP hydrolysis. This activity is critical during DNA replication and is a well characterized target for antibiotic inhibition of bacterial growth. In this assay, libraries of compounds are screened for inhibition of DNA gyrase. The assay measures the supercoiling of a relaxed plasmid by DNA gyrase as an electrophoretic shift on an agarose gel. Initially all libraries are screened for inhibitory activity at 30 μM and then a dose response analysis is effected with active compounds. Novobiocin, an antibiotic that binds to the β subunit of DNA gyrase is used as a positive control in the assay. The sensitivity of the DNA gyrase assay was determined by titrating the concentration of the know DNA gyrase inhibitor, Novobiocin, in the supercoiling assay. The $IC_{50}$ was determined to be 8 nM, sufficient to identify the activity of a single active species of comparable activity in a library having 30 μM concentration.

Assay 7: Metal chelator/imaging assay

This procedure is used to identify compounds of the invention from libraries of compounds constructed to include a ring that contains an ultraviolet chromophore. Further the chemical functional groups attached to the compounds of the invention are selected from metal binders, coordinating groups such as amine, hydroxyl and carbonyl groups, and other groups having lone pairs of electrons, such that the compounds of the invention can form coordination complexes with heavy metals and imaging agents. The procedure is used to identify compounds of the invention useful for chelating and removing heavy metals from industrial broths, waste stream eluents, heavy metal poisoning of farm animals and other sources of contaminating heavy metals, and for use in identifying imaging agent carriers, such as carriers for technetium 99.

An aliquot of a test solution having the desired ion or imaging agent at a known concentration is added to an aliquot of standard solution of the library under assay. The UV spectrum of this aliquot is measured and is compared to the UV spectrum of a further aliquot of the same solution lacking the test ion or imaging agent. A shift in the extinction coefficient is indicative of binding of the metal ion or imaging ion to a compound in the library being assayed.

Assay 8: $PLA_2$ inhibition assay

A target for assay of a combinatorially generated library of compounds is the phospholipase $A_2$ family. Phospholipases $A_2$ ($PLA_2$) are a family of enzymes that hydrolyze the sn-2 ester linkage of membrane phospholipids resulting in release of a free fatty acid and a lysophospholipid (Dennis, E. A., The Enzymes, Vol. 16, pp. 307–353, Boyer, P. D., ed., Academic Press, New York, 1983). Elevated levels of type II $PLA_2$ are correlated with a number of human inflammatory diseases. The $PLA_2$-catalyzed reaction is the rate-limiting step in the release of a number of pro-inflammatory mediators. Arachidonic acid, a fatty acid commonly linked at the sn-2 position, serves as a precursor to leukotrienes, prostaglandins, lipoxins and thromboxanes. The lysophospholipid can be a precursor to platelet-activating factor. $PLA_2$ is regulated by pro-inflammatory cytokines and, thus, occupies a central position in the inflammatory cascade (Dennis, ibid.; Glaser et al., TiPs Reviews 1992, 14, 92; and Pruzanski et al., Inflammation 1992, 16, 451). All mammalian tissues evaluated thus far have exhibited $PLA_2$ activity. At least three different types of $PLA_2$ are found in humans: pancreatic (type I), synovial fluid (type II) and cytosolic. Studies suggest that additional isoenzymes exist. Type I and type II, the secreted forms of $PLA_2$, share strong similarity with phospholipases isolated from the venom of snakes. The $PLA_2$ enzymes are important for normal functions including digestion, cellular membrane remodeling and repair, and in mediation of the inflammatory response. Both cytosolic and type II enzymes are of interest as therapeutic targets. Increased levels of the type II $PLA_2$ are correlated with a variety of inflammatory disorders including rheumatoid arthritis, osteoarthritis, inflammatory bowel disease and septic shock, suggesting that inhibitors of this enzyme would have therapeutic utility. Additional support for a role of $PLA_2$ in promoting the pathophysiology observed in certain chronic inflammatory disorders was the observation that injection of type II $PLA_2$ into the footpad of rats (Vishwanath et al., Inflammation 1988, 12, 549) or into the articular space of rabbits (Bomalaski et al., J. Immunol. 1991, 146, 3904) produced an inflammatory response. When the protein was denatured before injection, no inflammatory response was produced.

The type II $PLA_2$ enzyme from synovial fluid is a relatively small molecule (about 14 kD) and can be distinguished from type I enzymes (e.g. pancreatic) by the sequence and pattern of its disulfide bonds. Both types of enzymes require calcium for activity. The crystal structures of secreted $PLA_2$ enzymes from venom and pancreatic $PLA_2$, with and without inhibitors, have been reported (Scott et al., Science 1990, 250, 1541). Recently, the crystal structure of $PLA_2$ from human synovial fluid has been determined (Wery et al., Nature 1991, 352, 79). The structure clarifies the role of calcium and amino acid residues in catalysis. Calcium acts as a Lewis acid to activate the scissile ester carbonyl bond of 1,2-diacylglycerophospholipids and binds to the lipid, and a His-Asp side chain diad acts as a general base catalyst to activate a water molecule nucleophile. This is consistent with the absence of any acyl enzyme intermediates, and is also comparable to the catalytic mechanism of serine proteases. The catalytic residues and the calcium ion are at the end of a deep cleft (ca. 14 Å) in the enzyme. The walls of this cleft contact the hydrocarbon portion of the phospholipid and are composed of hydrophobic and aromatic residues. The positively-charged amino-terminal helix is situated above the opening of the hydrophobic cleft. Several lines of evidence suggest that the N-terminal portion is the interfacial binding site (Achari et al., Cold Spring Harbor Symp. Quant. Biol. 1987, 52, 441; Cho et al., J. Biol. Chem. 1988, 263, 11237; Yang et al., Biochem. J. 1989, 262, 855; and Noel et al., J. Am. Chem. Soc. 1990, 112, 3704).

Much work has been reported in recent years on the study of the mechanism and properties of $PLA_2$-catalyzed hydrolysis of phospholipids. In in vitro assays, $PLA_2$ displays a lag phase during which the enzyme adsorbs to the substrate bilayer and a process called interfacial activation occurs. This activation may involve desolvation of the enzyme/lipid interface or a change in the physical state of the lipid around the cleft opening. Evidence favoring this hypothesis comes from studies revealing that rapid changes in $PLA_2$ activity occur concurrently with changes in the fluorescence of a membrane probe (Burack et al., Biochemistry 1993, 32, 583). This suggests that lipid rearrangement is occurring during the interfacial activation process. $PLA_2$ activity is maximal around the melting temperature of the lipid, where regions of gel and liquid-crystalline lipid coexist. This is also consistent with the sensitivity of $PLA_2$ activity to temperature and to the composition of the substrate, both of which can lead to structurally distinct lipid arrangements separated by a boundary region. Fluorescence microscopy was used to simultaneously identify the physical state of the lipid and the position of the enzyme during catalysis (Grainger et al., FEBS Lett. 1989, 252, 73). These studies clearly show that $PLA_2$ binds exclusively at the boundary region between liquid and solid phase lipid. While the hydrolysis of the secondary ester bond of 1,2-diacylglycerophospholipids catalyzed by the enzyme is relatively simple, the mechanistic and kinetic picture is clouded by the complexity of the enzyme-substrate interaction. A remarkable characteristic of $PLA_2$ is that maximal catalytic activity is observed on substrate that is aggregated (i.e. phospholipid above its critical micelle concentration), while low levels of activity are observed on monomeric substrate. As a result, competitive inhibitors of $PLA_2$ either have a high affinity for the active site of the enzyme before it binds to the substrate bilayer or partition into the membrane and compete for the active site with the phospholipid substrate. Although a number of inhibitors appear to show promising inhibition of $PLA_2$ in biochemical assays (Yuan et al., J. Am. Chem. Soc. 1987, 109, 8071; Lombardo et al., J. Biol. Chem. 1985, 260, 7234; Washburn et al., J. Biol. Chem. 1991, 266, 5042; Campbell et al., J. Chem. Soc., Chem. Commun. 1988, 1560; and Davidson et al., Biochem. Biophys. Res. Commun. 1986, 137, 587), reports describing in vivo activity are limited (Miyake et al., J. Pharmacol. Exp. Ther. 1992, 263, 1302).

In one preferred embodiment, compounds of the invention are selected for their potential to interact with, and preferably inhibit, the enzyme $PLA_2$. Thus, compounds of the invention can be used for topical and/or systemic treatment of inflammatory diseases including a topic dermatitis and inflammatory bowel disease. In selecting the functional groups, advantage can be taken of $PLA_2$'s preference for anionic vesicles over zwitterionic vesicles. Preferred compounds of the invention for assay for $PLA_2$ include those having aromatic diversity groups to facilitate binding to the cleft of the $PLA_2$ enzyme (Oinuma et al., J. Med. Chem. 1991, 34, 2260; Marki et al., Agents Actions 1993, 38, 202; and Tanaka et al., J. Antibiotics 1992, 45, 1071). Benzyl and 4-hexylbenzyl groups are preferred aromatic diversity groups. $PLA_2$-directed compounds of the invention can further include hydrophobic functional groups such as tetraethylene glycol groups. Since the $PLA_2$ enzyme has a hydrophobic channel, hydrophobicity is believed to be an important property of inhibitors of the enzyme.

The libraries additionally can be screened in other in vitro assays to determine further mechanisms of inhibition. The libraries are screened for inhibition of $PLA_2$ in the assay using E. coli labeled with $^3$H-oleic acid (Franson et al., J. Lipid Res. 1974, 15, 380; and Davidson et al., J. Biol. Chem. 1987, 262, 1698) as the substrate. Type II $PLA_2$ (originally isolated from synovial fluid), expressed in a baculovirus system and partially purified, serves as a source of the enzyme. A series of dilutions of each of the libraries is performed: 10 $\mu$l of each library of compounds is incubated for 5 minutes at room temperature with a mixture of 10 $\mu$l $PLA_2$, 20 $\mu$l 5×$PLA_2$ Buffer (500 mM Tris 7.0–7.5, 5 mM $CaCl_2$), and 50 $\mu$l water. Samples of each library are run in duplicate. At this point, 10 $\mu$l of $^3$H E. coli cells is added. This mixture is incubated at 37° C. for 15 minutes. The enzymatic reaction is stopped with the addition of 50 $\mu$L 2M HCl and 50 $\mu$L fatty-acid-free BSA (20 mg/mL PBS), vortexed for 5 seconds, and centrifuged at high speed for 5 minutes. 165 $\mu$L of each supernate is then put into a scintillation vial containing 6 ml of scintillant (ScintiVerse) and cpms are measured in a Beckman Liquid Scintillation Counter. As a control, a reaction without the combinatorial pool (or library of compounds) is run alongside the other reactions as well as a baseline reaction containing no compounds of the invention as well as no $PLA_2$ enzyme. CPMs are corrected for by subtracting the baseline from each reaction data point.

Confirmation of the "winners" is made to confirm that a compound of the invention binds to enzyme rather than substrate and that the inhibition by a compound of the invention that is selected is specific for type II $PLA_2$. An assay using $^{14}$C-phosphatidyl ethanolamine ($^{14}$C-PE) as substrate, rather than *E. coli* membrane, is used to insure enzyme rather than substrate specificity. Micelles of $^{14}$C-PE and deoxycholate are incubated with the enzyme and a compound of the invention. $^{14}$C-labeled arachidonic acid released as a result of PLA$_2$-catalyzed hydrolysis is separated from substrate by thin layer chromatography and the radioactive product is quantitated. The "winner" is compared to phosphatidyl ethanolamine, the preferred substrate of human type II PLA$_2$, to confirm its activity. PLA2 from other sources (snake venom, pancreatic, bee venom) and phospholipase C, phospholipase D and lysophospholipase can be used to further confirm that the inhibition is specific for human type II PLA$_2$.

Assay 9: Leukotriene B$_4$ assay

Leukotriene B$_4$ (LTB$_4$) has been implicated in a variety of human inflammatory diseases, and its pharmacological effects are mediated via its interaction with specific surface cell receptors. Library products, either as discrete compounds or as small mixtures of compounds, are screened for competitive inhibition of radiolabeled LTB$_4$ binding to a receptor preparation.

A Nenques™ Drug Discovery System Kit (NEN Research Products, Boston, Mass.) is used to select an inhibitor of the interaction of Leukotriene B$_4$ (LTB$_4$) with receptors on a preparation of guinea pig spleen membrane. [$^3$H] Leukotriene B$_4$ reagent is prepared by adding 5 mL of ligand diluent (phosphate buffer containing NaCl, MgCl$_2$, EDTA and Bacitracin, pH 7.2) to 0.25 mL of the radioligand. The receptor preparation is made by thawing the concentrate, adding 35 mL of ligand diluent and swirling gently in order to re-suspend the receptor homogeneously. Reagents are kept on ice during the course of the experiment, and the remaining portions are stored at −20 C.

Library products prepared as per the general procedures of examples above are diluted to 5 μM, 50 μM and 500 μM in phosphate buffer (1×PBS, 0.1% azide and 0.1% BSA, pH 7.2), yielding final test concentrations of 0.5 μM, 5 μM and 50 μM, respectively. Samples are assayed in duplicate. [$^3$H] LTB$_4$ (25 μL) is added to 25 μL of either appropriately diluted standard (unlabeled LTB$_4$) or library product. The receptor suspension (0.2 mL) is added to each tube. Samples are incubated at 4 C for 2 hours. Controls include [$^3$H] LTB$_4$ without receptor suspension (total count vials), and sample of ligand and receptor without library molecules (standard).

After the incubation period, the samples are filtered through GF/B paper that had been previously rinsed with cold saline. The contents of each tube are aspirated onto the filter paper to remove unbound ligand from the membrane preparation, and the tubes washed (2×4 mL) with cold saline. The filter paper is removed from the filtration unit and the filter disks are placed in appropriate vials for scintillation counting. Fluor is added, and the vials shaken and allowed to stand at room temperature for 2 to 3 hours prior to counting. The counts/minute (cpm) obtained for each sample are subtracted from those obtained from the total counts to determine the net cpm for each sample. The degree of inhibition of binding for each library product is determined relative to the standard (sample of ligand and receptor without library product).

What is claimed is:
1. An amide compound of formula (I):

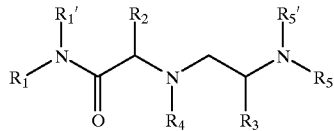

wherein:
each $R_1$, $R_{1'}$, $R_5$ and $R_{5'}$ is, independently, H, an amino protecting group, or CH$_2$, CH(R$_2$), C=O, C=S, S(=O)$_2$, C(=O)NH, C(=S)NH or C(=O)O substituted with H or a hydrocarbyl group selected from C$_1$–C$_{10}$ alkyl, C$_2$–C$_{10}$ alkenyl, C$_2$–C$_{20}$ alkynyl, C$_6$–C$_{14}$ aryl, C$_6$–C$_{14}$ aralkyl, C$_3$–C$_{14}$ cycloalkyl, C$_5$–C$_{14}$ fused cycloalkyl, C$_4$–C$_{14}$ heterocycle, C$_4$–C$_{14}$ heterocyclylalkyl, C$_4$–C$_{14}$ heteroaryl, C$_4$–C$_{14}$ heteroarylalkyl and CH(R$_2$)—NH—R$_2$; wherein said hydrocarbyl group is optionally substituted with oxo, acyl, alkoxy, alkoxycarbonyl, alkyl, alkenyl, alkynyl, amino, arnido, azido, aryl, heteroaryl, carboxylic acid, cyano, guanidino, halo, haloalkyl, haloalkoxy, hydrazino, hydroxyl, alkylsulfonyl, nitro, sulfide, sulfone, sulfonate, sulfonamide, thiol, and thioalkoxy, provided that $R_{1'}$ may also be a solid support;

each $R_4$ is Fmoc, Teoc, Bpoc, BOC, Alloc, Cbz, formyl, acetyl, trihaloacetyl, benzoyl, nitrophenylacetyl, 2-nitrobenzenesulfonyl, phthalimido, dithiasuccinyl, cytosine-1-acetyl, adenine-9-acetyl, guanine-9-acetyl, or CH$_2$, CH(R$_2$), C=O, C=S, S(=O)$_2$, C(=O)NH, C(=S)NH or C(=O)O substituted with H or a hydrocarbyl group selected from C$_1$–C$_{10}$ alkyl, C$_2$–C$_{10}$ alkenyl, C$_2$–C$_{20}$ alkynyl, C$_6$–C$_{14}$ aryl, C$_6$–C$_{14}$ aralkyl, C$_3$–C$_{14}$ cycloalkyl, C$_5$–C$_{14}$ fused cycloalkyl, C$_4$–C$_{14}$ heterocycle, C$_4$–C$_{14}$ heteroaryl, C$_4$–C$_{14}$ heteroarylalkyl and CH(R$_2$)—NH—R$_2$; wherein said hydrocarbyl group is optionally substituted with oxo, acyl, alkoxy, alkoxycarbonyl, alkyl, alkenyl, alkynyl, amino, amido, azido, aryl, heteroaryl, carboxylic acid, cyano, guanidino, halo, haloalkyl, haloalkoxy, hydrazino, hydroxyl, alkylsulfonyl, nitro, sulfide, sulfone, sulfonate, sulfonamide, thiol, and thioalkoxy; and each $R_2$ and $R_3$ is, independently, H or a hydrocarbyl group selected from C$_1$–C$_{10}$ alkyl, C$_2$–C$_{10}$ alkenyl, C$_2$–C$_{20}$ alkynyl, C$_6$–C$_{14}$ aryl, C$_6$–C$_{14}$ aralkyl, C$_3$–C$_{14}$ cycloalkyl, C$_5$–C$_{14}$ fused cycloalkyl, C$_4$–C$_{14}$ heterocyclyl, C$_4$–C$_{14}$ heterocycloalkyl, C$_4$–C$_{14}$ heteroaryl and C$_4$–C$_{14}$ heteroarylalkyl; wherein said hydrocarbyl group is optionally substituted with acyl, alkoxy, alkoxycarbonyl, alkyl, alkenyl, alkynyl, amino, amido, azido, aryl, heteroaryl, carboxylic acid, cyano, guanidino, halo, haloalkyl, haloalkoxy, hydrazino, hydroxyl, alkylsulfonyl, nitro, sulfide, sulfone, sulfonate, sulfonamide, thiol or thioalkoxy, provided that $R_2$ is not H.

2. The amide compound of claim 1 wherein said $R_1$ is benzyl, (2-aminoethyl)dimethyl, 1-(2-ethyl)imidazolidin-2-one, 2-pyridylmethyl, 1-(2-dimethylamino)ethyl or 2-(N-acetylamino)ethyl.

3. The amide compound of claim 1 wherein said $R_2$ is methyl, isobutyl, benzyl, 1-hydroxyethyl, carboxymethyl, aminomethyl, carbamoylmethyl, 2-carbamoylethyl, 3-(amidinoamino)propyl, 4-aminobenzyl, 2-aminomethyl, 3-indolylmethyl, imidazol-4-ylmethyl, hydroxymethyl, 4-aminobutyl, 2-carboxyethyl or 4-hydroxybenzyl.

4. The amide compound of claim 1 wherein said $R_3$ is hydrogen, hydroxymethyl, methyl, isobutyl, benzyl, 1-hydroxyethyl, 2-carboxyethyl, carboxymethyl, aminomethyl, 4-hydroxybenzyl, carbamoylmethyl, 2-carbamoylethyl, 3-(amidinoamino)propyl, 4-aminobenzyl, 2-aminoethyl, 3-indolylmethyl or imidazol-4-ylmethyl.

5. The amide compound of claim 1 wherein said $R_4$ is isonipecotyl, isobutyl, 3-pyridylmethyl, 3,5-bis-(trifluoromethyl)benzyl, hydantoyl, (2S)-2-amino-3-hydroxy-propionyl, nalidixoyl, 3-pyridylacetyl, cytosine-1-acetyl, adenine-9-acetyl, guanine-9-acetyl, thiophene-2-acetyl, hydroxyacetyl, 3-aminopropionyl or 6-quinolinecarboxyl.

6. The amide compound of claim 1 wherein said $R_5$ is hydrogen, (R)-(−)-2,2-dimethyl-5-oxo-1,3-dioxolane-4-acetyl, (2S)-2-amino-4-hydroxybutyryl, isonipecotyl, 3,5-diaminobenzoyl, (2S,3R)-2-amino-3-hydroxybutyryl, carbamoyl, carboxamidino, 1-fluorenecarboxyl, orotyl, nalidixoyl, 6-quinolinecarboxyl, thymine-1-acetyl, cytosine-1-acetyl, adenine-9-acetyl, guanine-9-acetyl, 3-(carbamoyl)benzoyl imidazole-4-carboxyl, hydroxyacetyl, nicotinoyl or 3-aminopropionyl.

7. The amide compound of claim 1 wherein said $R_{5'}$ is hydrogen.

8. An amide compound of formula (I):

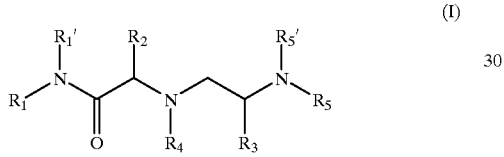

wherein:
each $R_1$, $R_{1'}$, $R_4$, $R_5$ and $R_{5'}$ is, independently, hydrogen, piperazinyl benzyl, 1-(2-ethyl)imidazolidin-2-one, 2-pyridylmethyl, 1-(2-dimethylamino)ethyl, 2-(N-acetylamino)ethyl, thiophene-2-acetyl, 3-aminopropionyl, 6-quinolinecarboxyl, nicotinoyl, 2-pyrazine-carboxyl, carboxamidino, 3-(trifluoromethyl)benzoyl, carbarnoyl, 2-aminopropionyl, imidazole-4-carboxyl, isonipecotyl, 3,5-diaminobenzoyl, isovaleryl, nalidixyl, 2-hydroxyacetyl, thymine-1-acetyl, aminocarbonyl, p-toluylsulfonyl, p-nitrophenylcarbonyl, p-toluylaminocarbonyl, 3,5-bis(trifluoromethyl)phenylcarbarnoyl, 3-pyridylmethyl, t-buty, N-ethyl-3-carbazolylmethyl, anthraquinone-2-carbonyl, isobutyl, nalidixoyl, p-t-butyl-phenycarbonyl, p-aminophenylcarbonyl, cyclopropyl-carbonyl, 2-nitrophenyl-sulfonyl, (R)-(−)-2,2-dimethyl-5-oxo-1,3-dioxolane-4-acetyl, (S)-(+)-2,2-dimethyl-5-oxo-1,3-dioxolane-4-acetyl, carboxamidino, 2,6-dichloroisonicotinyl, carbamoylmethyl, 3-pyridylmethyl, 5-hydantoinacetyl, 2-amino-4-hydroxybutyryl, benzo[c]1,2,5-oxadiazole-5-carboxyl, hydantoyl, niflumyl, orotyl and 2-phenylacetyl, provided that $R_{1'}$ may also be a solid support and $R_4$ is not hydrogen; and each $R_2$ and $R_3$ is, independently, H or a hydrocarbyl group selected from $C_1$–$C_{10}$ alkyl, $C_2$–$C_{10}$ alkenyl, $C_2$–$C_{20}$ alkynyl, $C_6$–$C_{14}$ aryl, $C_6$–$C_{14}$ aralkyl, $C_3$–$C_{14}$ cycloalkyl, $C_5$–$C_{14}$ fused cycloalkyl, $C_4$–$C_{14}$ heterocyclyl, $C_4$–$C_{14}$ heterocycloalkyl, $C_4$–$C_{14}$ heteroaryl and $C_4$–$C_{14}$ heteroarylalkyl; wherein said hydrocarbyl group is optionally substituted with acyl, alkoxy, alkoxycarbonyl, alkyl, alkenyl, alkynyl, amino, amido, azido, aryl, heteroaryl, carboxylic acid, cyano, guanidino, halo, haloalkyl, haloalkoxy, hydrazino, hydroxyl, alkylsulfonyl, nitro, sulfide, sulfone, sulfonate, sulfonamide, thiol or thioalkoxy, provided that $R_2$ is not H.

9. An amide compound of formula (I):

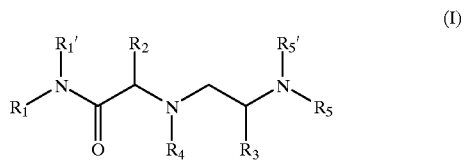

wherein:
each $R_1$, $R_{1'}$, $R_4$, and $R_{5'}$ is, independently, hydrogen, piperazinyl, benzyl, 1-(2-ethyl)imidazolidin-2-one, 2-pyridylmethyl, 1-(2-dimethylamino)ethyl, 2-(N-acetylamino)ethyl, thiophene-2-acetyl, 3-aminopropionyl, 6-quinolinecarboxyl, nicotinoyl, 2-pyrazine-carboxyl, carboxamidino, 3-(trifluoromethyl)benzoyl, carbamoyl, 2-aminopropionyl, imidazole-4-carboxyl, isonipecotyl), 3,5-diaminobenzoyl, isovaleryl, nalidixyl, 2-hydroxyacetyl, thymine-1-acetyl, aminocarbonyl, p-toluylsulfonyl, p-nitrophenylcarbonyl, p-toluylaminocarbonyl, 3,5-bis(trifluoromethyl)phenylcarbamoyl, 3-pyridylmethyl, t-butyl, N-ethyl-3-carbazolylmethyl, anthraquinone-2-carbonyl, isobutyl, nalidixoyl, p-t-butyl-phenycarbonyl, p-aminophenylcarbonyl, cyclopropyl-carbonyl, 2-nitrophenyl-sulfonyl, (R)-(−)-2,2-dimethyl-5-oxo-1,3-dioxolane-4-acetyl, (S)-(+)-2,2-dimethyl-5-oxo-1,3-dioxolane-4-acetyl, carboxamidino, 2,6-dichloroisonicotinyl, carbamoylmethyl, 3-pyridylmethyl, 5-hydantoinacetyl, 2-amino-4-hydroxybutyryl, benzo[c]1,2,5-oxadiazole-5-carboxyl, hydantoyl, niflumyl, orotyl and 2-phenylacetyl, provided that $R_{1'}$ may also be a solid support and $R_4$ is not hydrogen;

$R_3$ is hydrogen, (R)-(−)-2,2-dimethyl-5-oxo-1,3-dioxolane-4-acetyl, (2S)-2-amino-4-hydroxybutyryl, isonipecotyl, 3,5-diaminobenzoyl, (2S,3R)-2-amino-3-hydroxybutyryl, carbamoyl, carboxamidino, 1-fluorenecarboxyl, orotyl, nalidixoyl, 6-quinolinecarboxyl, thymine-1-acetyl, cytosine-1-acetyl, adenine-9-acetyl, guanine-9-acetyl, 3-(carbamoyl)benzoyl, imidazole-4-carboxyl, 2-hydroxyacetyl, nicotinoyl or 3-aminopropionyl; and each $R_2$ and $R_3$ is, independently, H or a hydrocarbyl group selected from $C_1$–$C_{10}$ alkyl, $C_2$–$C_{10}$ alkenyl, $C_2$–$C_{20}$ alkryl, $C_6$–$C_{14}$ aryl, $C_6$–$C_{14}$ aralkyl, $C_3$–$C_{14}$ cycloalkyl, $C_5$–$C_{14}$ fused cycloalkyl, $C_4$–$C_{14}$ heterocyclyl, $C_4$–$C_{14}$ heterocycloalkyl, $C_4$–$C_{14}$ heteroaryl and $C_4$–$C_{14}$ heteroarylalkyl; wherein said hydrocarbyl group is optionally substituted with acyl, alkoxy, alkoxycarbonyl, alkyl, alkenyl, alkynyl, amino, amido, azido, aryl, heteroaryl, carboxylic acid, cyano, guanidino, halo, haloalkyl, haloalkoxy, hydrazino, hydroxyl, alkylsulfonyl, nitro, sulfide, sulfone, sulfonate, sulfonamide, thiol or thioalkoxy, provided that $R_2$ is not H.

* * * * *